US011022603B2

(12) United States Patent
Beckwith et al.

(10) Patent No.: US 11,022,603 B2
(45) Date of Patent: Jun. 1, 2021

(54) MICROFLUIDIC TISSUE BIOPSY AND IMMUNE RESPONSE DRUG EVALUATION DEVICES AND SYSTEMS

(71) Applicants: The Charles Stark Draper Laboratory, Inc., Cambridge, MA (US); Massachusetts Institute of Technology, Cambridge, MA (US)

(72) Inventors: Ashley Lynne Beckwith, Cambridge, MA (US); Jeffrey Borenstein, Newton, MA (US); Nathan Moore, Canton, MA (US); Daniel Doty, Arlington, MA (US); Luis Velasquez-Garcia, Cambridge, MA (US)

(73) Assignees: THE CHARLES STARK DRAPER LABORATORY, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 231 days.

(21) Appl. No.: 16/116,656

(22) Filed: Aug. 29, 2018

(65) Prior Publication Data
US 2019/0064148 A1 Feb. 28, 2019

Related U.S. Application Data

(60) Provisional application No. 62/552,264, filed on Aug. 30, 2017, provisional application No. 62/581,667, filed on Nov. 4, 2017.

(51) Int. Cl.
*G01N 33/50* (2006.01)
*C12M 1/32* (2006.01)
(Continued)

(52) U.S. Cl.
CPC .... *G01N 33/5008* (2013.01); *B01L 3/502761* (2013.01); *C12M 23/12* (2013.01);
(Continued)

(58) Field of Classification Search
CPC . C12M 23/16; C12M 23/12; B01L 3/502761; B01L 2300/0816;
(Continued)

(56) References Cited

U.S. PATENT DOCUMENTS

2004/0037739 A1* 2/2004 McNeely ................ B01L 9/527
422/417
2007/0092901 A1* 4/2007 Ligler ................... B01L 3/5027
435/6.11

(Continued)

FOREIGN PATENT DOCUMENTS

EP 3647405 A1 * 5/2020 ........ B01L 3/502761

OTHER PUBLICATIONS

International Search Report and Written Opinion for PCT/US2018/048592 dated Jan. 23, 2019.

*Primary Examiner* — Michael L Hobbs
(74) *Attorney, Agent, or Firm* — Foley & Lardner LLP

(57) ABSTRACT

This disclosure describes microfluidic tissue biopsy and immune response drug evaluation devices and systems. A microfluidic device can include an inlet channel having a first end configured to receive a fluid sample optionally containing a tissue sample. The microfluidic device can also include a tissue trapping region at the second end of the inlet channel downstream from the first end. The tissue trapping region can include one or more tissue traps configured to catch a tissue sample flowing through the inlet channel such that the fluid sample contacts the tissue trap. The microfluidic device can also include one or more channels providing an outlet.

29 Claims, 17 Drawing Sheets

(51) Int. Cl.
*B01L 3/00* (2006.01)
*C12M 3/06* (2006.01)

(52) U.S. Cl.
CPC .... *G01N 33/5082* (2013.01); *B01L 2200/027* (2013.01); *B01L 2200/0668* (2013.01); *B01L 2200/0684* (2013.01); *B01L 2300/0816* (2013.01); *B01L 2300/0864* (2013.01); *B01L 2300/0877* (2013.01); *B01L 2300/0883* (2013.01); *B01L 2400/0463* (2013.01); *B01L 2400/0487* (2013.01); *B01L 2400/086* (2013.01); *C12M 23/16* (2013.01)

(58) Field of Classification Search
CPC ..... B01L 2300/0864; B01L 2300/0883; B01L 2300/0877; B01L 2200/0668; B01L 2200/0684; B01L 2400/0463; B01L 2400/0487; B01L 2400/086; G01N 33/5008; G01N 33/5082
See application file for complete search history.

(56) References Cited

U.S. PATENT DOCUMENTS

| | | |
|---|---|---|
| 2014/0093953 A1 | 4/2014 | Ingram |
| 2015/0018226 A1 | 1/2015 | Hansen |
| 2015/0352547 A1* | 12/2015 | Breinlinger ........... B01L 3/5027 435/395 |
| 2016/0236195 A1* | 8/2016 | Daridon ................. C12M 21/06 |
| 2016/0237476 A1 | 8/2016 | Meldrum |

* cited by examiner

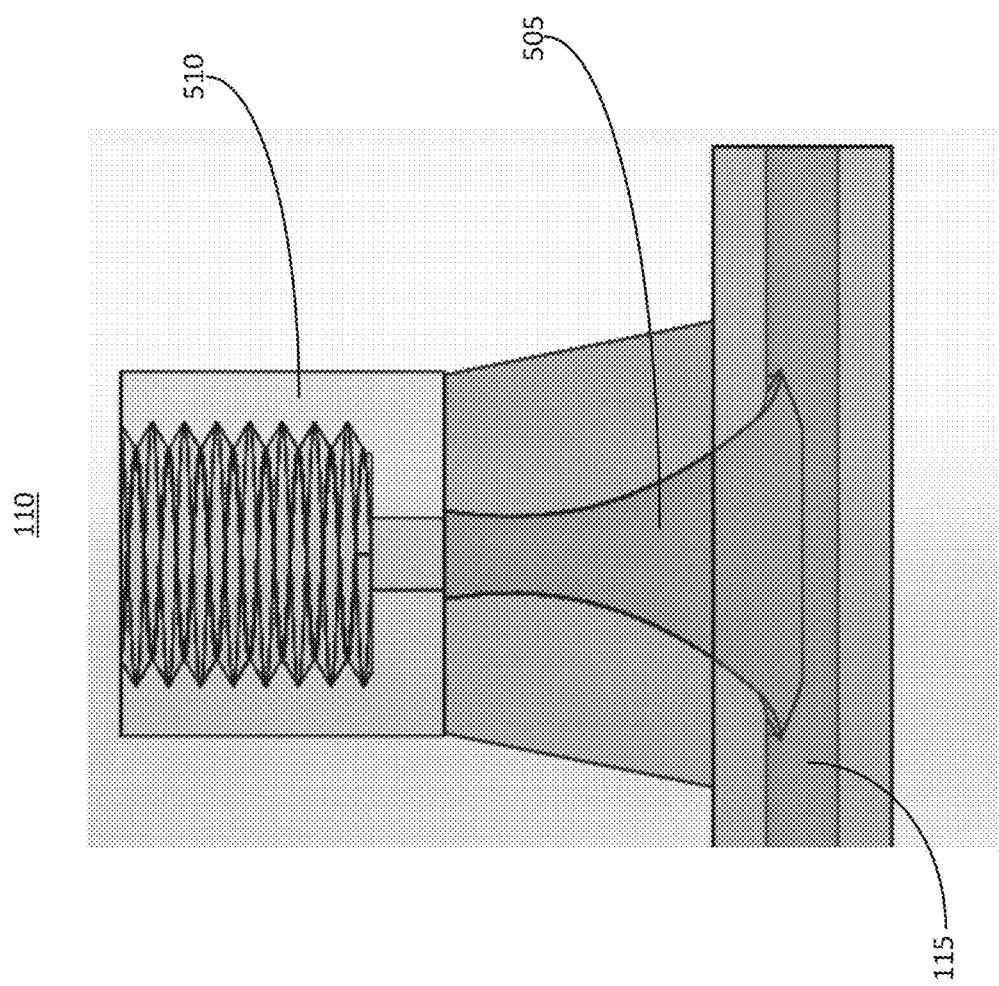

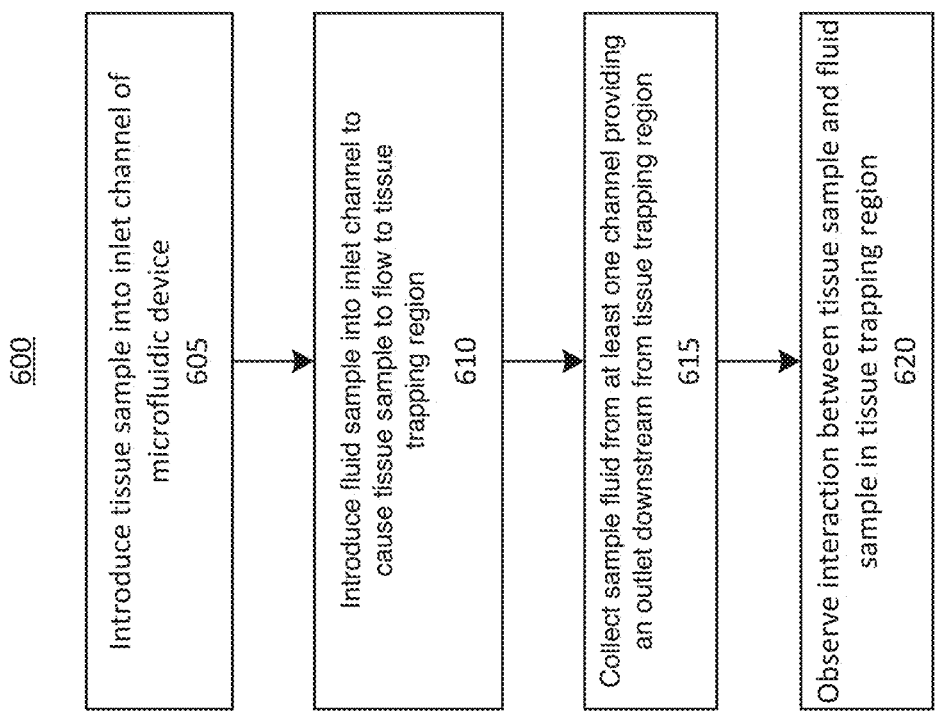

MICROFLUIDIC TISSUE BIOPSY AND IMMUNE RESPONSE DRUG EVALUATION DEVICES AND SYSTEMS

CROSS-REFERENCE TO RELATED APPLICATIONS

The present application claims priority to U.S. Provisional Patent Application 62/552,264, filed Aug. 30, 2017 and titled "MICROFLUIDIC TISSUE BIOPSY AND IMMUNE RESPONSE DRUG EVALUATION DEVICES AND SYSTEMS," and to U.S. Provisional Patent Application 62/581,667, filed Nov. 4, 2017 and titled "MICROFLUIDIC TISSUE BIOPSY AND IMMUNE RESPONSE DRUG EVALUATION DEVICES AND SYSTEMS," each of which is incorporated herein by reference in its entirety.

BACKGROUND

Current technology for simulating dynamic processes involving interactions between mammalian tissue samples and cells is gated by the inability to recapitulate the tissue microenvironment and interactions between tissues, therapeutic compounds and the host immune system.

SUMMARY

One aspect of this disclosure is directed to microfluidic device comprising including a substrate. The substrate defines an inlet channel having a first end configured to receive a fluid sample optionally containing a tissue sample. The substrate defines a tissue trapping region at the second end of the inlet channel downstream from the first end. The tissue trapping region includes one or more tissue traps configured to catch a tissue sample flowing through the inlet channel such that the fluid sample contacts the tissue trap. The substrate also defines one or more channels providing an outlet.

In some implementations, at least one of the one or more tissue traps comprises an arrangement of one or more walls. In some implementations, the one or more channels providing the outlet include one or more branch channels connecting to the second end of the inlet channel where the second end of the inlet channel and the tissue trapping region converge. In some implementations, the convergence of the second end of the inlet channel and the tissue trapping region further includes a first branch channel coupled to the second end of the inlet channel at a first junction and configured to direct a first portion of the fluid sample in a first direction, and a second branch channel coupled to the second end of the inlet channel at the first junction and configured to direct a second portion of the fluid sample in a second direction, different form the first direction, wherein the tissue trap is positioned at the first junction.

In some implementations, the one or more channels providing the outlet further include one or more suction channels downstream of the one or more tissue traps and configured to hold the tissue sample in place within the one or more tissue traps. In some implementations, at least one of the one or more tissue traps includes a bottom surface positioned at a lower depth than a bottom surface of the inlet channel. In some implementations, the first branch channel and the second branch channel converge at a second junction downstream from the one or more tissue traps.

In some implementations, the microfluidic device further includes a first suction channel coupling at least one of the one or more tissue traps to the first branch channel at a third junction downstream from the second end of the inlet channel. The microfluidic device can also include a second suction channel coupling the at least one of the one or more tissue traps to the second branch channel at a fourth junction downstream from the second end of the inlet channel. In some implementations, a diameter of at least one of the one or more the tissue traps is about twice that of the inlet channel.

In some implementations, the tissue trapping region includes a ribbed channel coupling the inlet channel to the one or more channels providing the outlet. In some implementations, at least one of the one or more tissue traps can be defined by sidewalls of ribs of the ribbed channel and a bottom wall positioned at a lowest depth of the ribbed channel. In some implementations, the at least one tissue trap can further include at least a second tissue trap and a third tissue trap.

In some implementations, the tissue trapping region can include a circuitous channel having a first curved portion coupled to the second end of the inlet channel. The microfluidic device can also include at least one of the one or more tissue traps positioned at a center of the first curved portion such that the fluid sample flows along the first curved portion past the tissue trap. In some implementations, the one or more channels providing the outlet channel can include a suction channel coupling to the at least one of the one or more tissue traps and configured to carry the fluid sample downstream from the at least one of the one or more tissue traps. In some implementations, the circuitous channel can further include a second curved portion coupled to a downstream end of the first curved portion and a second tissue trap positioned at a center of the second curved portion such that the fluid sample flows along the second curved portion past the second tissue trap. In some implementations, a downstream end of the second curved portion is coupled to the one or more channels providing the outlet.

In some implementations, the microfluidic device can also include an inlet port coupled to the first end of the inlet channel and configured to deliver the fluid sample to the inlet channel. In some implementations, the inlet port can include a first threaded connector configured for attachment to a fluid line.

In some implementations, the microfluidic device can also include a bubble trapping structure coupled to the inlet channel downstream from the inlet port. The bubble trapping structure can be configured to facilitate evacuation of air bubbles from the fluid sample. In some implementations, a surface of the bubble trapping structure can have a shape defined by a parabolic function. In some implementations, the bubble trapping structure can further include a second threaded connector configured for attachment to an air release line.

In some implementations, the microfluidic device can also include an outlet port coupled to the at least one of the one or more channels providing the outlet and configured to remove the fluid sample from the microfluidic device. In some implementations, the substrate can be formed from a biocompatible material. In some implementations, the substrate can be formed from an optically transparent material, and the microfluidic device can further include an optical interface providing optical access to the tissue sample positioned within the tissue trapping region. In some implementations, the one or more tissue traps can be configured to entrain the tissue sample in place within the one or more tissue traps.

Another aspect of this disclosure is directed to a method for evaluating an interaction between a tissue sample and a fluid sample. The method can include introducing a tissue sample into a first end of an inlet channel of a microfluidic device. The method can include introducing a fluid sample into the first end of the inlet channel to cause the tissue sample to flow to a tissue trapping region at a second end of the inlet channel downstream from the first end. The tissue trapping region can include a tissue trap configured to catch the tissue sample such that at least a portion of the fluid sample contacts the tissue sample. The method can include collecting the sample fluid from at least one channel providing an outlet downstream from the tissue trapping region.

In some implementations, the method can include priming the inlet channel with fluid prior to introducing the tissue sample into the first end of the inlet channel. In some implementations, the method can include observing an interaction between the tissue sample and the fluid sample in the tissue trapping region. In some implementations, the microfluidic device can be formed from a transparent material, and observing the interaction between the tissue sample and the fluid sample can further include positioning a lens of a microscope in proximity to the microfluidic device.

In some implementations, the tissue trap can be configured to secure the tissue sample without damaging the tissue sample. In some implementations, the method can include introducing the tissue sample via a bubble trapping structure coupled to the inlet channel, and introducing the fluid sample via an inlet port coupled to the inlet channel. The inlet port can be upstream from the bubble trapping structure. In some implementations, the method can include removing air from the fluid sample via the bubble trapping structure.

In some implementations, the method can include releasing the tissue sample from the tissue trap by introducing a second fluid sample into at least one of the one or more channels configured to provide the outlet such that the second fluid sample flows towards the inlet channel.

In some implementations, after collecting the sample fluid at least one of the one or more channels configured to provide the outlet downstream from the tissue trapping region, the method can include reintroducing the collected sample fluid into the inlet channel of the microfluidic device.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing.

FIG. 5 illustrates a bubble trapping structure that can be included in the microfluidic device of FIG. 1A, according to an illustrative implementation.

FIG. 6 illustrates a flowchart of a method for evaluating an interaction between a tissue sample and a fluid sample, according to an illustrative implementation.

DETAILED DESCRIPTION

Figure 1A:
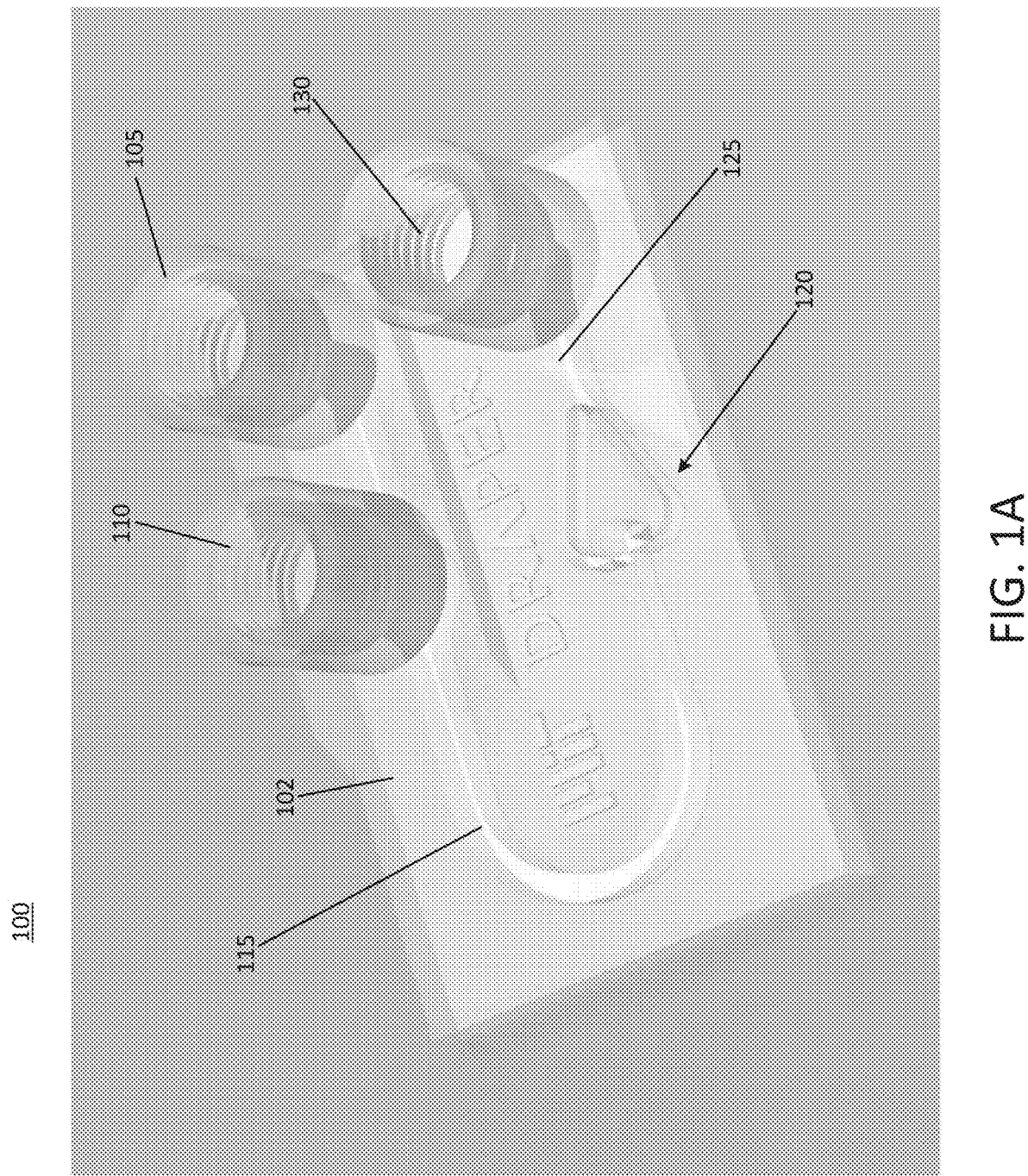
FIG. 1A illustrates a perspective view of an example microfluidic device, according to an illustrative implementation.

This disclosure aims to establish a robust platform to recapitulate the tissue microenvironment and interactions with host immune cells.

This disclosure describes devices and systems capable of recapitulating the tissue microenvironment and tissue interactions with fluid which may contain cells (such as circulating immune cells), medications, therapeutic compounds, or other components. As used herein, "fluid" can refer to fluid containing components that are intended to interact with a tissue sample (such as cells, medications, therapeutic compounds, or other substances) in order to observe a response, or can refer to fluid devoid of such components. A key challenge in this regard is the ability to maintain a tissue sample, such as a tumor biopsy, in a configuration that permits real-time observation of tumor viability and responses to therapeutic compounds, such as dynamic interactions between circulating immune cells and the tissue biopsy sample. This disclosure describes multiple novel designs capable of capturing and maintaining the position of a tissue sample in a flow field that presents cells, medications, therapeutic compounds, or other components to the tissue in a physiologically relevant manner, permitting control over perfusion rates and shear forces to ensure that results are relevant to human in vivo conditions.

Beyond the tissue trapping and flow field device, in order to fully recapitulate the dynamics of tissue interactions with cells such as immune cells, medications, therapeutic compounds, or other components, and to do so in a high throughput manner, it can be useful to integrate the device with a system capable of sustaining the tissue, maintaining control over the flow rate, viability of cells and density of circulating components, and to avoid problems common to microfluidic systems such as bubbles, debris, blockages or variability in flow rates. A key challenge is the ability to integrate these features in a manner that provides robust control over system dynamics for periods of up to one week or more.

In some implementations, the devices of this disclosure are capable of ex vivo simulation of the dynamics of tissue interactions with various fluid components, such as cells, medications, or therapeutic compounds. The devices can integrate capture regions, cell flow channels, resistance lines and fluidic connections, and bubble trapping structures. The devices described herein can permit observation and control over interactions between various types of fluid components and excised tissues such as tumor biopsy samples, skin biopsies, epithelial tissues such as gut, airway, renal or reproductive tract tissues. The figures and corresponding description below provide further detailed information regarding the design of such devices and systems. In brief, this disclosure includes various aspects, including specific designs for tissue traps, including a heart-shaped branching structure, ribbed channel bottom structure, S-curve structure, and suction port structure. Each serves as a means to precisely control and freeze the position of a tissue biopsy sample in a flow stream, and to expose the fixed tissue sample to a precisely controlled flow of fluid containing components such as cells, medications, or therapeutic compounds in order to observe interactions between the fluid components and tissue samples. This disclosure also includes aspects relating to integration of these trapping devices with other fluidic components. These additional components can include resistance channels, fluidic connectors and branch points, tissue sample loading ports, bubble trapping structures, drug dosing and media sampling ports, cell containment vessels, and manifolds that serve as distribution branches for cells and gas pressure lines.

For tissue trapping regions, other ways to address the problem include the use of V-shaped posts to trap tissues, side chamber regions, or side-to-side channels with cells flowing through one lane and tissues held in another, with a gel region in between. Additional potential designs for these systems include methods where the biopsied tissue sample is contained within a side channel or side compartment that indirectly receives flow from the main dynamic perfusion channel, methods where excised biopsy samples are contained within larger excised tissues or organs, or methods where biopsy samples are contained within constructs that are molded from mammalian tissues.

In other implementations, interactions between fluid and tissues can be mimicked by generating tissue constructs contained within gel or matrix regions. Fluid can flow through adjacent channels in which they are permitted to migrate toward the matrix-embedded tissue constructs. Some such devices and systems can utilize conventional microwell plates or transwells to contain excised tissues, as a static representation of the cell-tissue interaction.

The devices of this disclosure include innovative aspects in the nature of the tissue trapping geometry as compared to other approaches that may use V-shaped posts, side chambers, or side-to-side channels with intervening gel regions. The disadvantages of these approaches relate to the inability to precisely control the rate at which circulating fluid are presented to the tissue biopsy sample, because V-shaped post regions require dealing with a tradeoff between allowing flow around the tissue and raising the hydrostatic pressure of flow against the tissue sample. For side chambers or side-to-side channels, tissue interactions with fluid can occur via migration phenomena, which may be difficult to control in the microenvironment, or by random "strikes" of fluid traveling obliquely through the flow stream. This disclosure provides novel designs that can be used to contain tissue biopsy samples and channels for flowing fluid.

Other approaches to solving the tissue-cell interaction problem include using conventional means to contain tissues and fluid (e.g., static wells or transwells) and/or gel-matrix systems in which tissue samples are disaggregated and seeded into microfluidic devices in compartments adjacent to blood/cell-flow channels. Technical obstacles to the innovations described herein include developing designs capable of capturing tissue biopsy samples and effectively causing interaction of these captured samples with flowing media. These innovative concepts are not obvious because they include new tissue biopsy sample containment designs that overcome previous limitations. Key advantages of the devices and systems of this disclosure include designs that effectively entrain tissue biopsy samples and expose them to flowing fluid in a manner that optimizes the cross-section of interaction between the two.

Figure 1B:
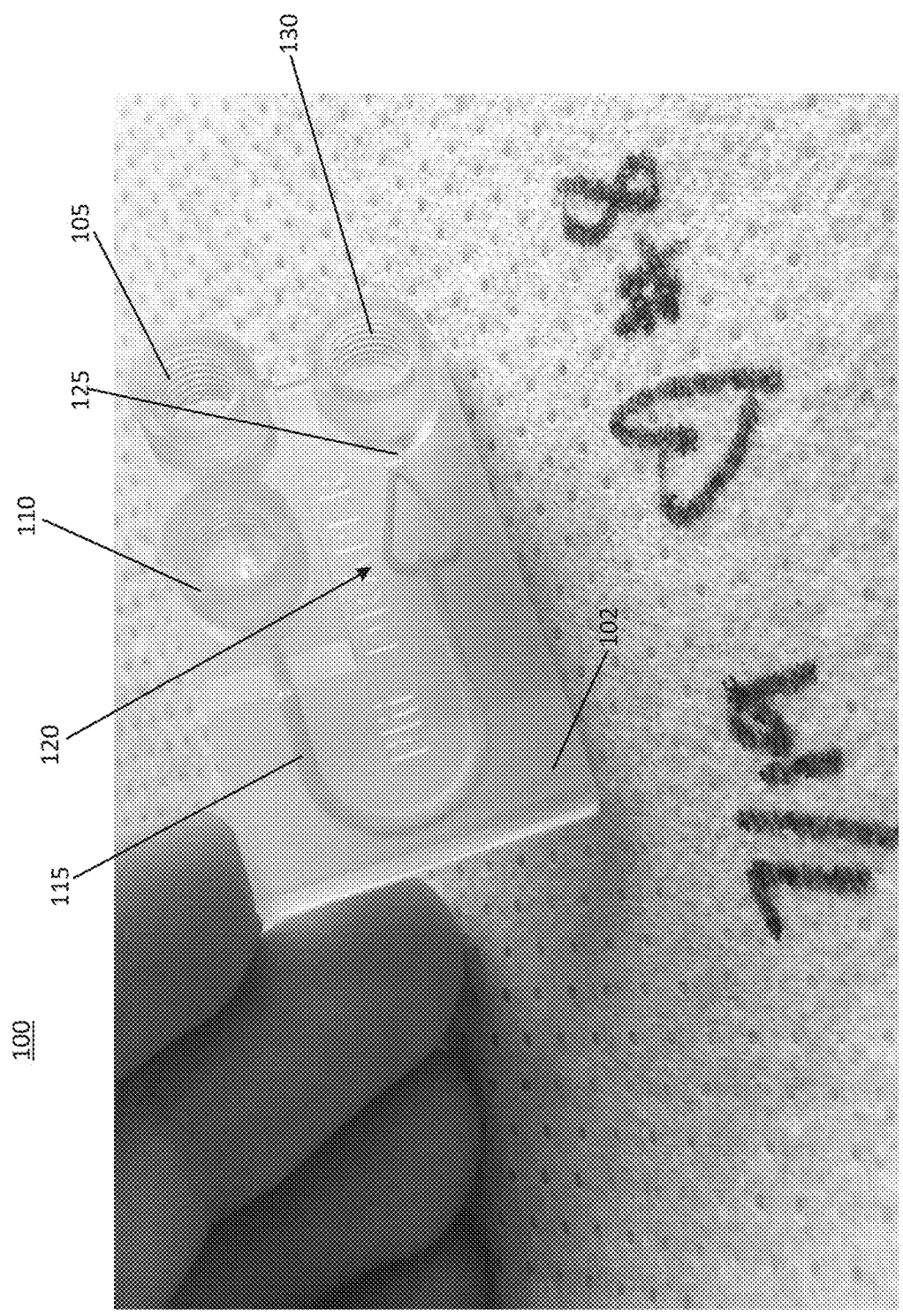
FIG. 1B illustrates a second perspective view of the example microfluidic device of FIG. 1A, according to an illustrative implementation.

FIG. 1A illustrates a perspective view of an example microfluidic device 100, according to an illustrative implementation. FIG. 1B illustrates a second perspective view of the example microfluidic device 100 of FIG. 1A. Similar reference numerals in FIGS. 1A and 1B refer to similar elements. Referring to both FIG. 1A and FIG. 1B, the microfluidic device 100 can be used to simulate interactions between tumors or other tissue samples and the immune system, for example by providing a microenvironment for testing the effectiveness of immunotherapy treatments on lymphocytes and tumor biopsies taken directly from a patient. As a result, the microfluidic device 100 can be used to model the in vivo environment and analyze the prolonged response of a tumor and circulating lymphocytes to the controlled introduction of immunotherapy pharmaceuticals. Thus, the microfluidic device 100 can enables judicious administration of immunotherapy treatments by allowing medical professionals to make informed decisions regarding course of treatment for a patient based on experiments conducted using the microfluidic device 100.

The microfluidic device 100 is formed from a substrate 102. The substrate 102 defines a variety of structural features, including an inlet port 105 leading to an inlet channel 115. Downstream from the inlet port 105 and coupled to the inlet channel 115 is a bubble trapping structure 110. Farther downstream from the inlet channel 115 is a tissue trapping region 120, which leads to an outlet channel 125. An outlet port 130 is positioned at a downstream end of the outlet channel 125. While only a single microfluidic device 100 is depicted in FIGS. 1A and 1B, it should be understood that in some implementations, multiple devices similar to the microfluidic device 100 can be incorporated into a single chip without departing from the scope of this disclosure.

In use, the microfluidic device 100 can capture a tissue sample and allow testing of the interaction of the tissue sample with various cells, medications, therapeutic compounds, or other agents or components included within a fluid sample flowing within the microfluidic device 100. For example, a tissue sample, such as a portion of a tumor, can be loaded into the device via the inlet port 105 or via the bubble trapping structure 110. After the tissue sample flows through the inlet channel 115, the structural characteristics of the tissue trapping region 120 cause the tissue sample to become trapped. A fluid sample can then be introduced into the inlet port 105 and flowed through the inlet channel 115, while the tissue sample remains held in place in the tissue trapping region 120. At least a portion of the fluid sample (and the cells, medications, therapeutic compounds, or other components within the sample) can contact the trapped tissue sample as it flows from the inlet channel 115 to the outlet channel 125 and finally exits the microfluidic device 100 via the outlet port 130. In some implementations, air bubbles that may be present in the fluid sample, and which may cause damage to the tissue sample or may otherwise interfere with the results of the experiment, can be removed from the microfluidic device 100 via the bubble trapping structure 110.

It should be understood that, in the implementation shown in FIG. 1A, the outlet channel 125 serves as an outlet for the microfluidic device 100 as a whole, but not for the tissue trapping region 120. Thus, in some implementations, the outlet channel 125 may not be an outlet channel relative to the tissue trapping region 120, and therefore may be referred to by a different name. In some implementations, one or more channels may provide an outlet for fluid at or near the tissue trapping region 120. For example, branching channels, suction channels, and other channels further described below may provide such an outlet. Thus, in some implementations, these channels also may be referred to as outlet channels. Various types of channels that may provide an outlet for fluid at or near the tissue trapping region 120 are described further below.

In some implementations, the microfluidic device 100 can be further configured to provide an optical interface for viewing the interaction site where the tissue sample interacts with the fluid sample. To facilitate optical access, the channels within the microfluidic device 100 can be configured to substantially avoid optical distortion. In some implementations, the channels can have a rounded rectangular cross-sectional shape. Such a shape exhibits smaller surface area to volume ratio than a purely rectangular channel, which can help to preserve pumping efficiency by reducing resistance in the channels. In addition, rounded rectangular channels may not produce image distortion that is characteristic of channels having circular cross-sectional shapes.

These and other aspects of this disclosure are described further below. In particular, a variety of different geometries and structural shapes can be used to implement the tissue trapping region 120, and several examples of such geometries are shown in the figures. In particular, FIGS. 2A-2F generally relate to a first geometry for the tissue trapping region 120, FIGS. 3A and 3B generally relate to a second geometry for the tissue trapping region 120, and FIGS. 4A-4D generally relate to a third geometry for the tissue trapping region 120.

Figure 2A:
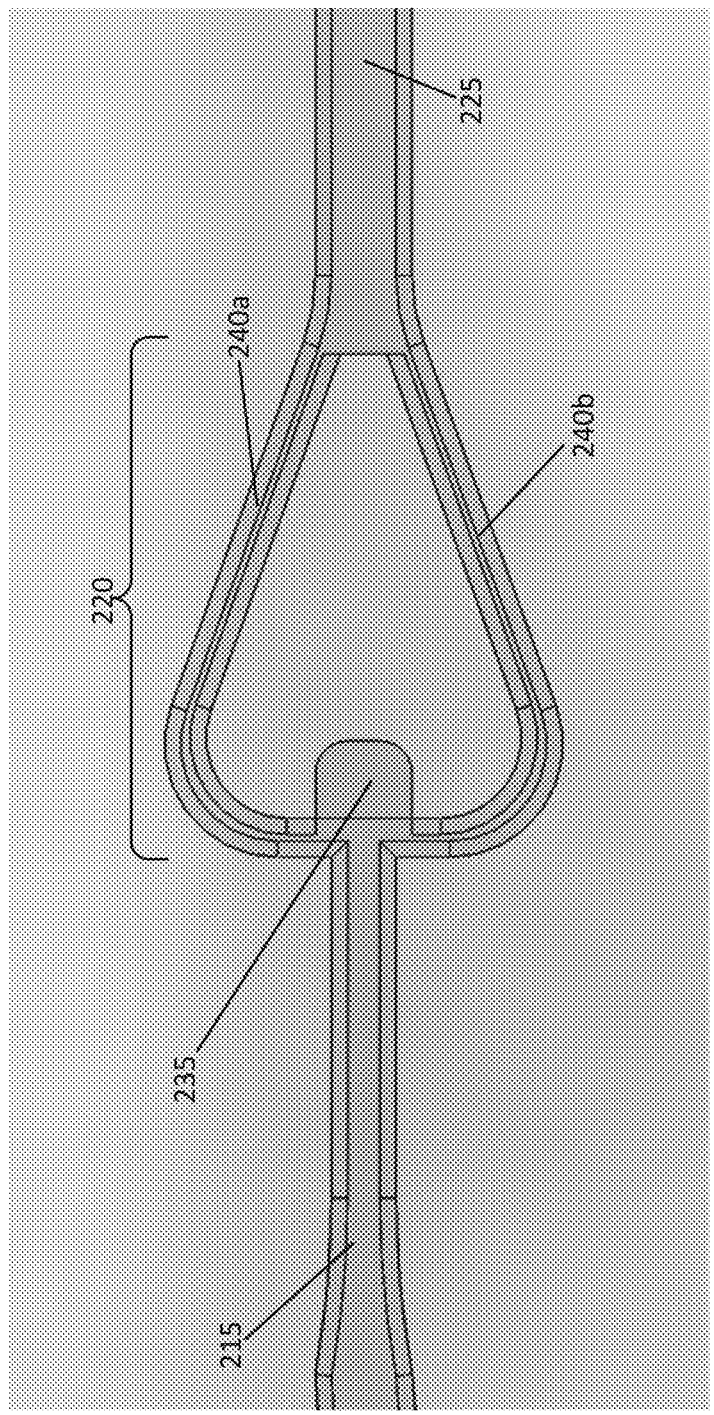
FIG. 2A illustrates a cross-sectional view of a portion of an example microfluidic device that can be used to implement the microfluidic device of FIG. 1A, according to an illustrative implementation.

FIG. 2A illustrates a cross-sectional view of a portion of an example microfluidic device 200 that can be used to implement the microfluidic device 100 of FIG. 1A, according to an illustrative implementation. The features of the microfluidic device 200 generally correspond to the features of the microfluidic device 100, and like reference numerals refer to like elements. For example, the microfluidic device 200 includes an inlet channel 215, a tissue trapping region 220, and an outlet channel 225 that can carry fluid out of the microfluidic device 200. FIG. 2 shows the structural details of the tissue trapping region 220, which in this example includes a tissue trap (also referred to as a tissue trapping zone or trapping zone) 235 positioned at a downstream end of the inlet channel 215, as well as two branch channels 240a and 240b branching off from the inlet channel 215 in opposing directions at a junction near the tissue trap 235.

Figure 2B:
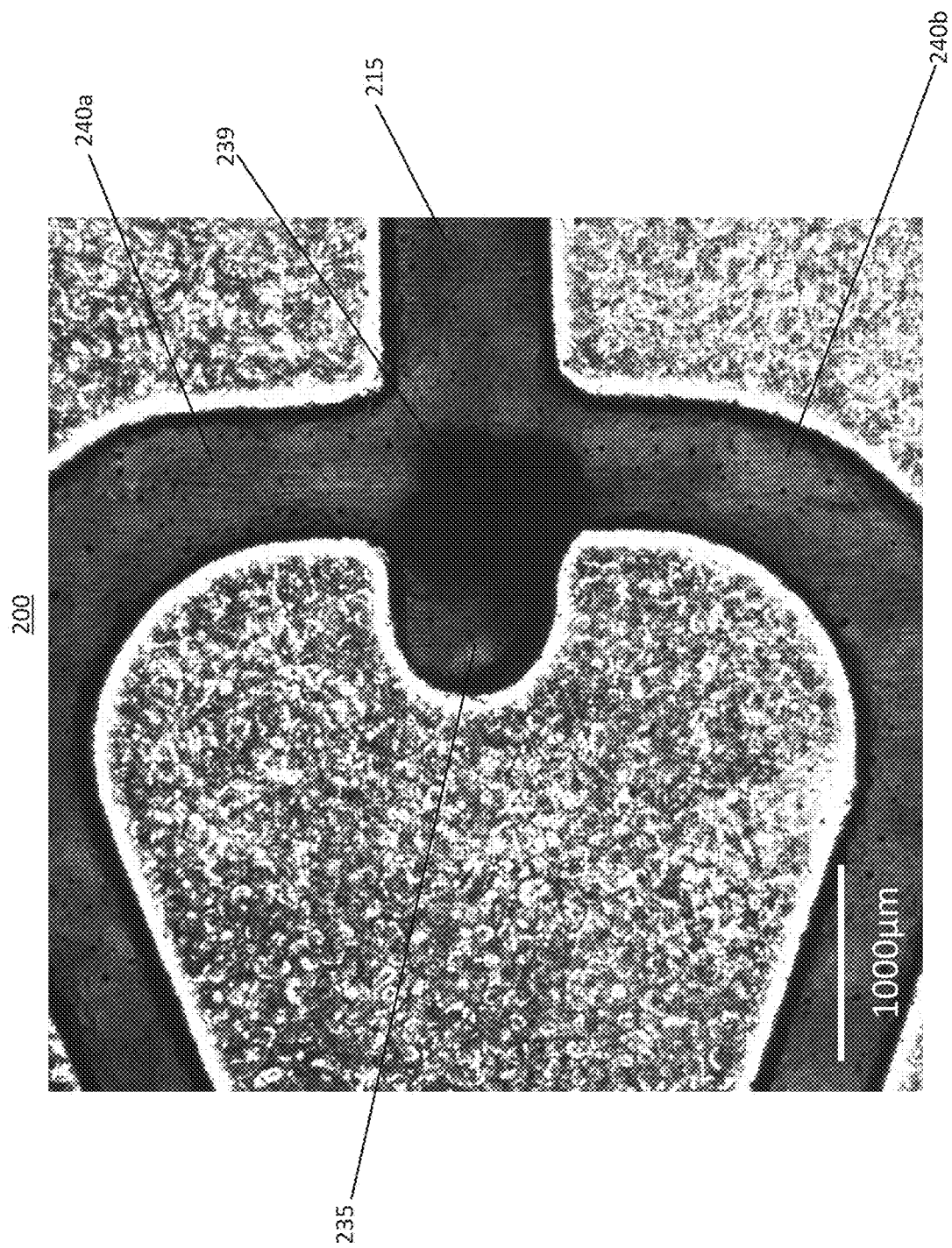
FIG. 2B illustrates a tissue sample within the microfluidic device of FIG. 2A, according to an illustrative implementation.

As described above, the tissue trapping region 220 is configured to trap a tissue sample in a fixed location while a fluid sample is flowed through the microfluidic device 200. For example, in some implementations, the tissue trapping region 220 is shaped such that, when the fluid sample flows through the microfluidic device 200, a stagnation zone exists in at least a portion of the area of the tissue trap 235, causing the tissue sample to become trapped in the tissue trap 235. FIG. 2B illustrates a tissue sample 239 within the microfluidic device 200 of FIG. 2A, according to an illustrative implementation. It should be noted that FIG. 2B shows the microfluidic device 200 in a reversed orientation relative to that shown in FIG. 2A, such that fluid flows from right to left in the depiction of the microfluidic device 200 of FIG. 2B. As shown, the tissue sample 239 becomes trapped in the tissue trap 235 in a manner that allows the fluid sample to continue flowing through the inlet channel 215 to the branch channels 240a and 240b, while a portion of the fluid sample contacts the tissue sample 239 as it flows.

Figure 2C:
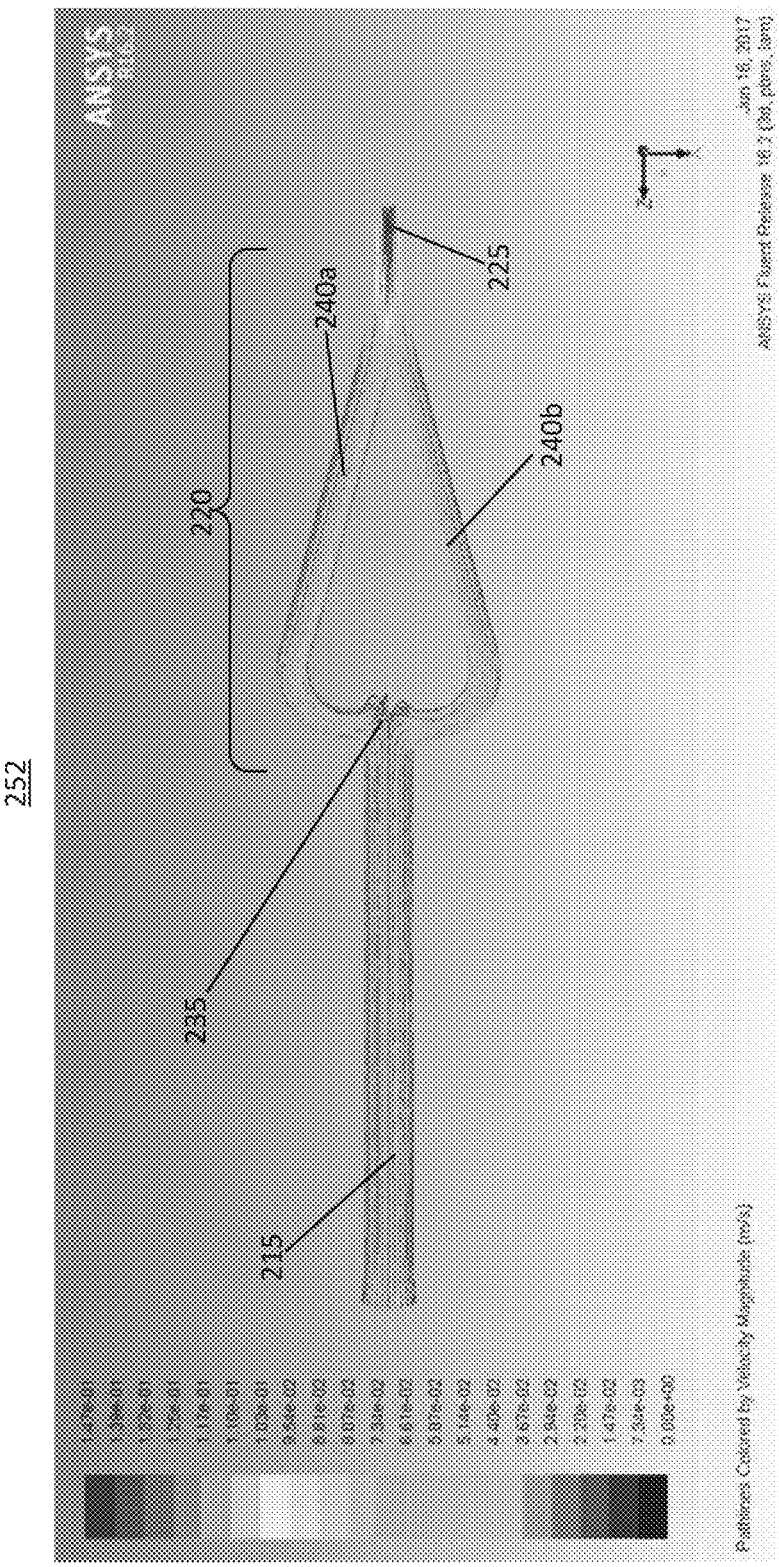
FIG. 2C is a visual depiction of the flow characteristics of the microfluidic device of FIG. 2A, according to an illustrative implementation.

In some implementations, the tissue trap or trapping zone 235 can have a bottom wall that is positioned at a lower depth than the bottom of the inlet channel 215 that leads up to it. That is, the tissue trap 235 can be stepped down relative to the bottom surface of the inlet channel 215. Thus, the tissue trap 235 can serve as a pocket for catching, trapping, holding, immobilizing, or securing the tissue sample 239. In some implementations, the shape of the tissue trapping region 220, including the tissue trap 235, is selected to catch or otherwise facilitate trapping of the tissue sample 239 while the fluid sample passes through the microfluidic device 200. For example, the tissue trap 235 can have a diameter that is larger than that of the inlet channel 215. In some implementations, the tissue trap 235 can have a diameter that is about twice that of the inlet channel 215. FIG. 2C is a visual depiction 252 of the flow characteristics of the microfluidic device 200 of FIG. 2A, according to an illustrative implementation. The shading within the channels shows the velocity of the streamlines within the device. When the streamlines bend at the branch channels 240a and 240b, the inertia of the tissue sample can overcome the viscous forces and can become lodged in the tissue trap 235.

Referring again to FIG. 2B, the trapping of the tissue sample 239 in a manner that allows the fluid sample to continue flowing through the device while contacting the tissue sample 239 can allow the interactions between the tissue sample 239 and agents within the fluid sample. For example, in some implementations fluorescent materials can be added to either the fluid sample or the tissue sample 239, and the visual characteristics of the tissue sample 239 and the fluid sample can be observed over time. To facilitate such observation, the microfluidic device 200 can be formed from a material that is transparent and optically clear, at least in the region of the device near the tissue trap 235. This area can serve as an optical interface that can be examined by an optical instrument, such as a camera or a microscope, that is brought into proximity with the microfluidic device 200.

Figure 2D:
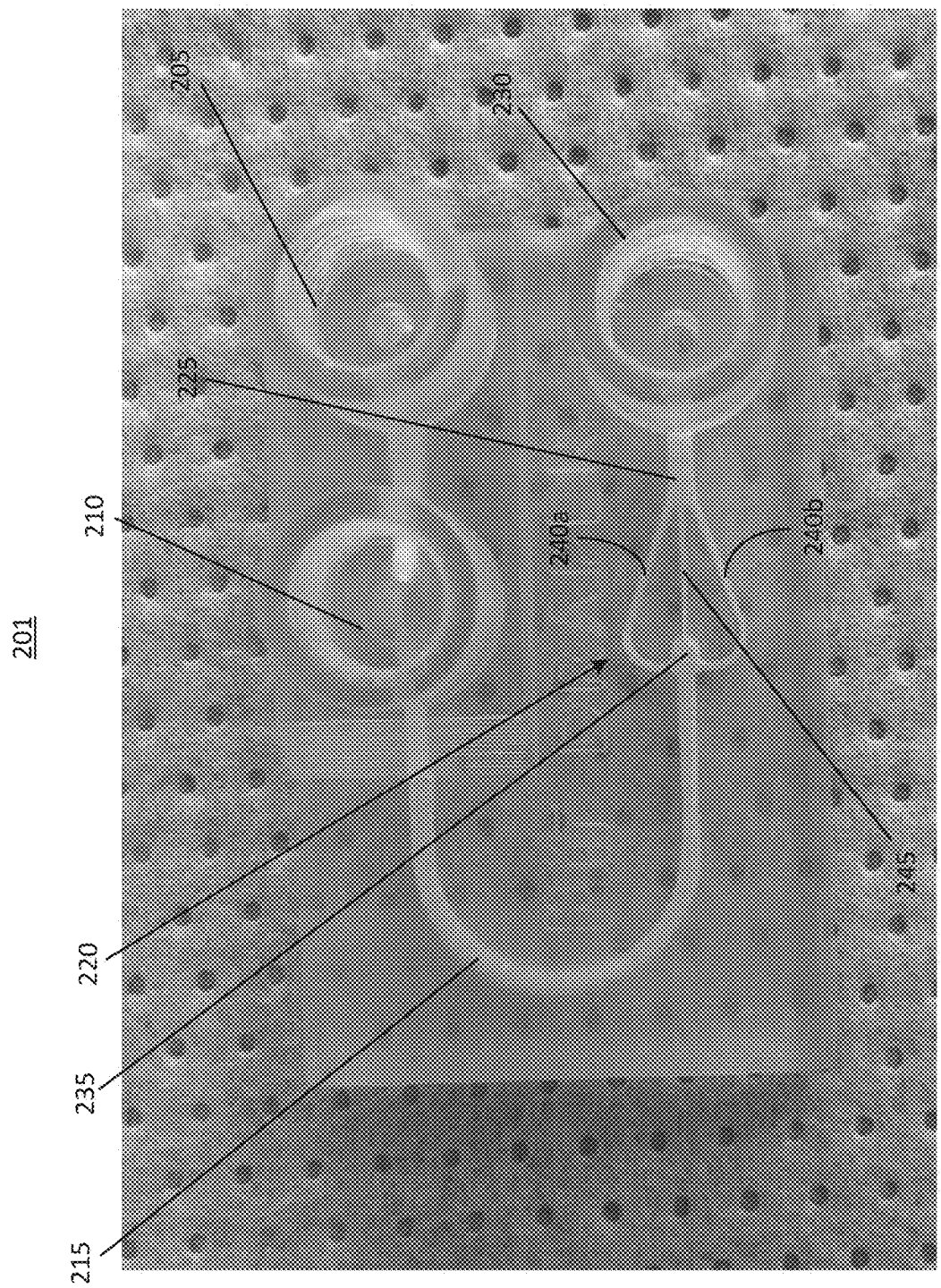
FIG. 2D illustrates a first arrangement of the microfluidic device of FIG. 2A having suction channels, according to an illustrative implementation.

FIG. 2D illustrates a first arrangement 201 of the microfluidic device of FIG. 2A having suction channels, according to an illustrative implementation. Components shown in the arrangement 201 are substantially similar to the components shown in FIG. 2A, and like reference numerals refer to like elements. However, the arrangement 201 of FIG. 2D differs from that shown in FIG. 2A in that the arrangement 201 includes a suction channel 245. The suction channel 245 is coupled between a downstream end of the tissue trap 235 and the outlet channel 225. Thus, the suction channel 245 can provide an outlet for fluid in the tissue trap 235, and therefore may sometimes itself be referred to as an outlet channel. Similarly, the microfluidic device 201 also includes branch channels 240a and 240b that can provide an outlet for fluid near the tissue trap 235, and therefore the branch channels 240a and 240b may also be referred to as outlet channels 240a and 240b. Furthermore, it should be understood that the outlet channel provides an outlet of the microfluidic device 201 (i.e., it is configured to carry fluid out of the microfluidic device 201), but does not couple to the tissue trap 235 and therefore does not serve as an outlet for fluid from the tissue trap 235. In some implementations, the suction channel 245 can be configured to facilitate trapping of the tissue sample within the tissue trap 235. For example, as the fluid sample flows from left to right in the depiction of FIG. 2D, through the branch channels 240a and 240b and into the outlet channel 225, the suction channel 245 can create a pressure drop or suction effect that tends to cause the tissue sample to be forced towards the right-hand side of the tissue trap 235, thereby becoming lodged within the tissue trap 235 more forcefully.

Figure 2E:
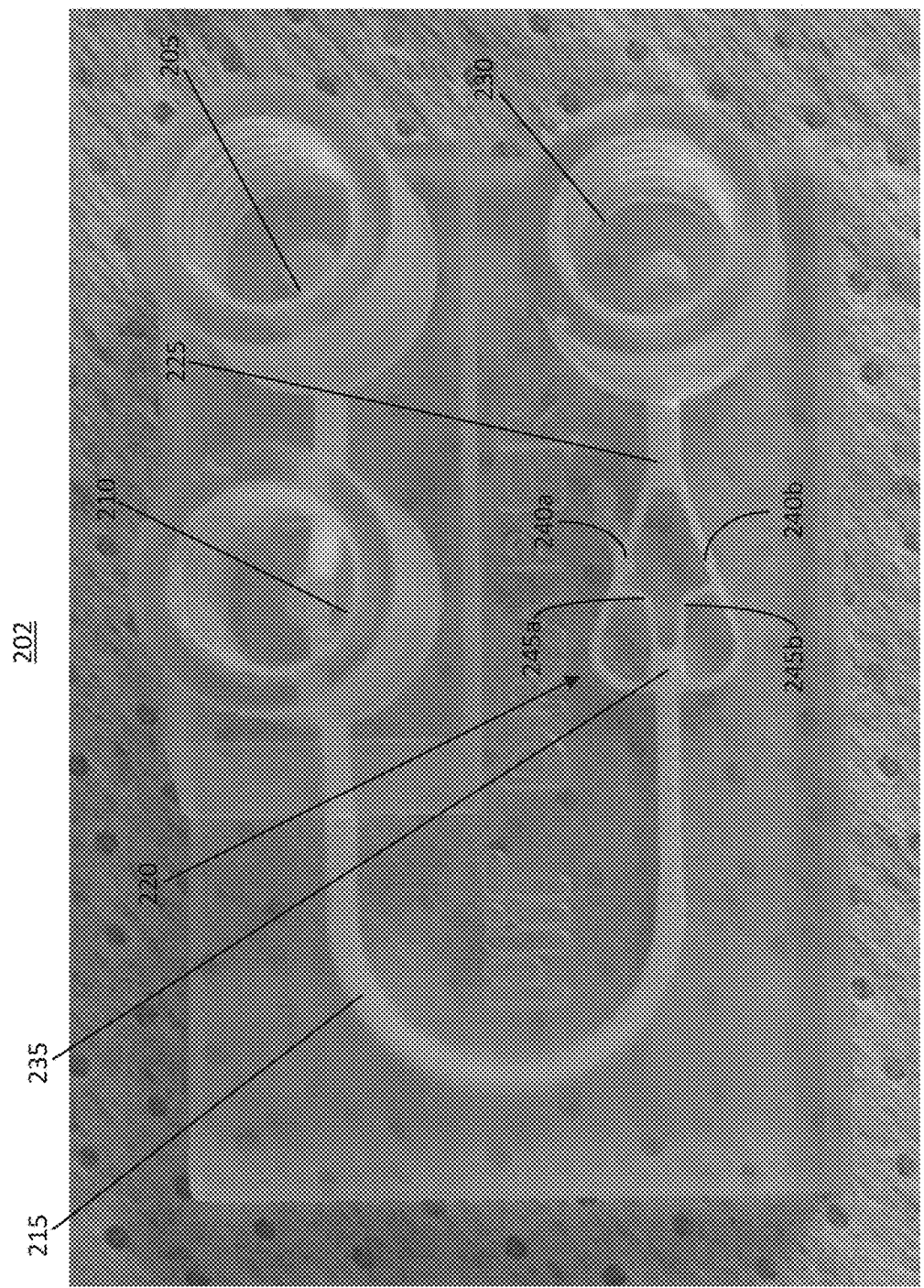
FIG. 2E illustrates a second arrangement of the microfluidic device of FIG. 2A having suction channels, according to an illustrative implementation.

FIG. 2E illustrates a second arrangement 202 of the microfluidic device of FIG. 2A having suction channels, according to an illustrative implementation. Components shown in the arrangement 202 are substantially similar to the components shown in FIG. 2A, and like reference numerals refer to like elements. However, the arrangement 202 of FIG. 2E differs from that shown in FIG. 2A in that the arrangement 202 includes two suction channels 245a and 245b. The suction channels 245a and 245b are coupled between a downstream end of the tissue trap 235 and the branch channels 240a and 240b, respectively. In some implementations, the suction channels 245a and 245b can be configured to facilitate trapping of the tissue sample within the tissue trap 235, in a manner similar to that of the suction channel 245 shown in FIG. 2D. For example, as the fluid sample flows from left to right in the depiction of FIG. 2E, through the branch channels 240a and 240b, the suction channels 245a and 245b can create a pressure drop or suction effect that tends to cause the tissue sample to be forced towards the right-hand side of the tissue trap 235, thereby becoming lodged within the tissue trap 235 more forcefully. In addition, because the suction channels 245a and 245b couple directly to a downstream end of the tissue trap 235, the suction channels 245a and 245b can provide an outlet for fluid in the tissue trap 235. Therefore, in some implementations the suction channels 245a and 245b may sometimes be referred to as outlet channels.

Figure 2F:
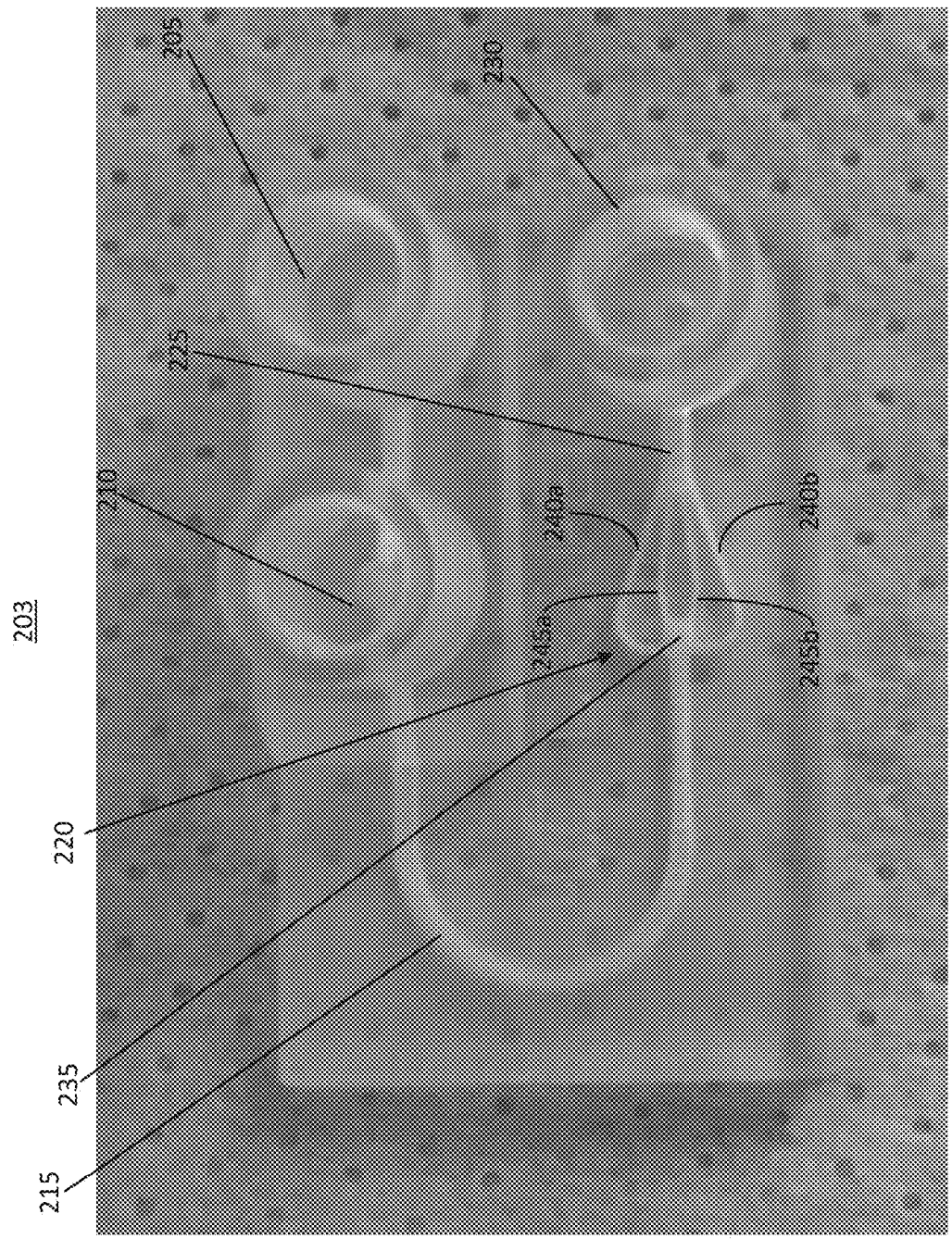
FIG. 2F illustrates a third arrangement of the microfluidic device of FIG. 2A having suction channels, according to an illustrative implementation.

Similarly, FIG. 2F illustrates a third arrangement 203 of the microfluidic device of FIG. 2A having suction channels 245a and 245b, according to an illustrative implementation. The arrangement 203 of FIG. 2F is similar to the arrangement 202 of FIG. 2E, with the exception that the suction channels 245a and 245b in the arrangement 203 couple to a junction of the branch channels 240a, 240b, and the outlet channel 225. However, the suction channels 245a and 245b in the arrangement 203 serve a similar purpose to that described above in connection with FIG. 2E. That is, as the fluid sample flows from left to right in the depiction of FIG. 2F, through the branch channels 240a and 240b and into the outlet channel 225, the suction channels 245a and 245b can create a pressure drop or suction effect that tends to cause the tissue sample to be forced towards the right-hand side of the tissue trap 235, thereby becoming lodged within the tissue trap 235 more forcefully. The suction channels 245a and 245b couple directly to a downstream end of the tissue trap 235, thereby providing an outlet for fluid in the tissue trap 235. Therefore, in some implementations the suction channels 245a and 245b may sometimes be referred to as outlet channels.

Figure 3A:
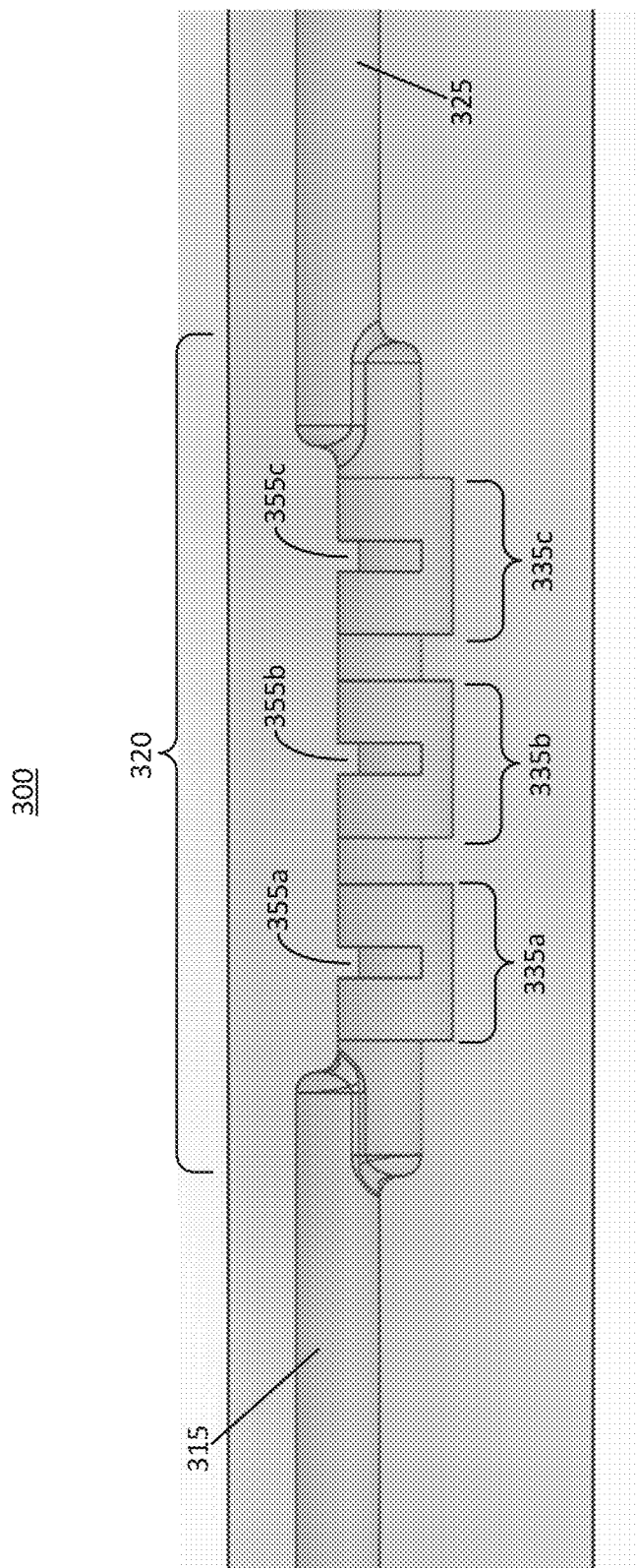
FIG. 3A illustrates a cross-sectional view of a portion of an example microfluidic device that can be used to implement the microfluidic device of FIG. 1A, according to an illustrative implementation.
Figure 3B:
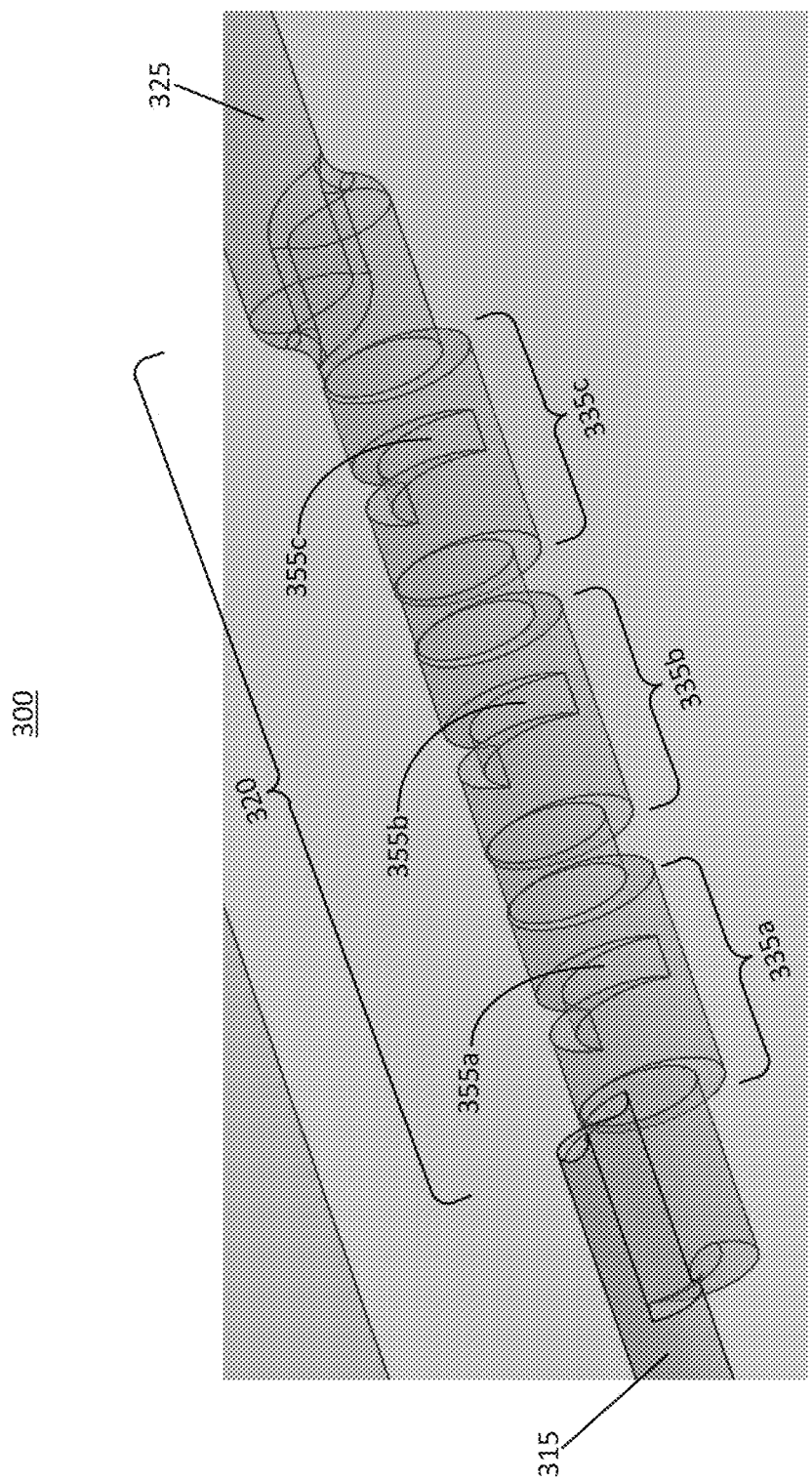
FIG. 3B illustrates a perspective view of the portion of the microfluidic device shown in FIG. 3A, according to an illustrative implementation.

FIG. 3A illustrates a cross-sectional view of a portion of an example microfluidic device 300 that can be used to implement the microfluidic device of FIG. 1A, according to an illustrative implementation. FIG. 3B illustrates a perspective view of the portion of the microfluidic device 300 shown in FIG. 3A. The features of the microfluidic device 300 generally correspond to the features of the microfluidic device 100, and like reference numerals refer to like elements. For example, the microfluidic device 300 includes an inlet channel 315, a tissue trapping region 320, and an outlet channel 325. FIGS. 3A and 3B show the structural details of the tissue trapping region 320, which in this example includes a ribbed channel coupled between the inlet channel 315 and the outlet channel 325. The ribbed channel includes ribs, such as the ribs 355a-355c (generally referred to as ribs 355), that project into the ribbed channel. The ribbed channel also defines tissue traps 335a-335c (generally referred to as tissue traps 335).

In general, each of the tissue traps 335 has sidewalls defined by a subset of the ribs 355. As shown, the bottom wall of each tissue trap 335 is positioned at a lowest depth of the ribbed channel, which is lower than the bottom wall of the inlet channel 315 and the outlet channel 325. While the depiction of FIG. 3A shows the ribbed channel defining three tissue traps 355, it should be understood that, in other implementations, the ribbed channel may include any number of ribs 355 defining any number of tissue traps 335 without departing from the scope of this disclosure.

Similar to the tissue trapping region 220 shown in FIG. 2A, the tissue trapping region 320 (including the tissue traps 335) can be configured to trap a tissue sample in a fixed location while a fluid sample is flowed through the microfluidic device 300. For example, the tissue trapping region 320 is shaped such that, when the fluid sample flows through the microfluidic device 300, the tissue sample becomes trapped in the tissue traps 335. In some implementations, a separate tissue sample can become trapped in each of the tissue traps 335. In some other implementations, one or more of the tissue traps 335 may remain unused for a given experiment.

Figure 3C:
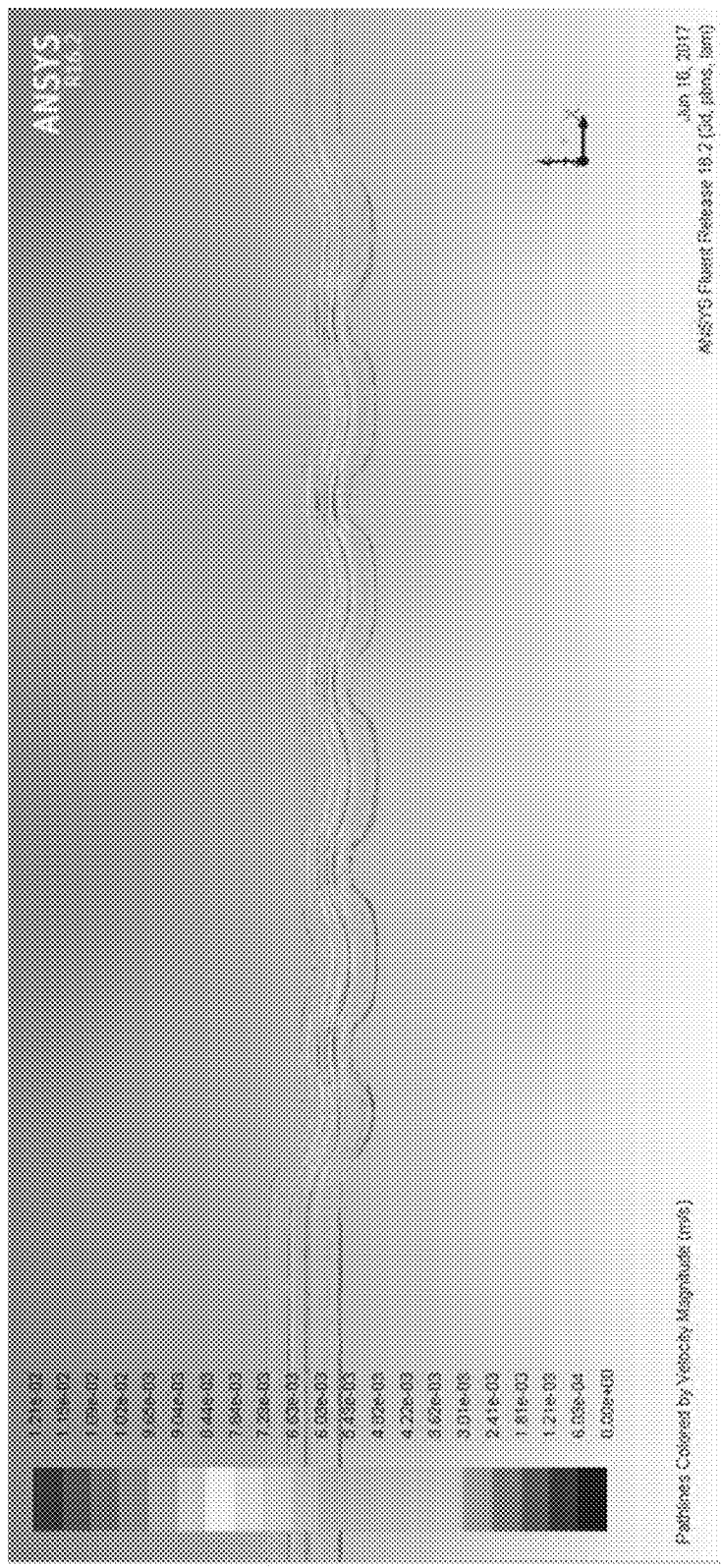
FIG. 3C is a visual depiction of the flow characteristics of the microfluidic device of FIG. 3A, according to an illustrative implementation.

In some implementations, the ribbed shape of the tissue trapping region 320, including the tissue traps 335, is selected to facilitate trapping of a tissue sample while the fluid sample passes through the microfluidic device 300. FIG. 3C is a visual depiction 352 of the flow characteristics of the microfluidic device 300 of FIG. 3A, according to an illustrative implementation. The shading within the channels shows the velocity of the streamlines within the microfluidic device 300. Generally, a tissue sample will be larger and heavier than other particles that flow through the device 300 within the fluid sample. As a result, the tissue sample will tend to sink within the flow due to gravity. Thus, positioning the tissue traps 335 at the lowest depth of the ribbed channel, which includes small obstructing ribs 355, can help to cause the tissue sample to become trapped within one of the tissue traps 335.

It should be understood that the microfluidic device 300 can include any of the features and functionality described above with respect to the microfluidic device 100 and the microfluidic device 200 shown in FIGS. 1A and 2A, respectively. For example, the microfluidic device 300 can be formed from a material that is transparent and optically clear in the region of the device near the tissue traps 335, which can serve as an optical interface that can be examined by an optical instrument brought into proximity with the microfluidic device 300. As a result, the tissue samples and the fluid sample in the tissue traps 335 can be observed optically over time.

It should be understood that, in the implementation shown in FIG. 3A, the outlet channel 325 serves as an outlet for the microfluidic device 100 as a whole, and also for the tissue trapping region 120. In some implementations, although not illustrated in FIG. 3A, the microfluidic device 300 also may include one or more additional channels that serve as outlets for fluid at or near the tissue trapping region 320, which may also be referred to as outlet channels. For example, such channels may be branch channels or suction channels similar to those described above in connection with FIGS. 2D-2F.

Figure 4A:
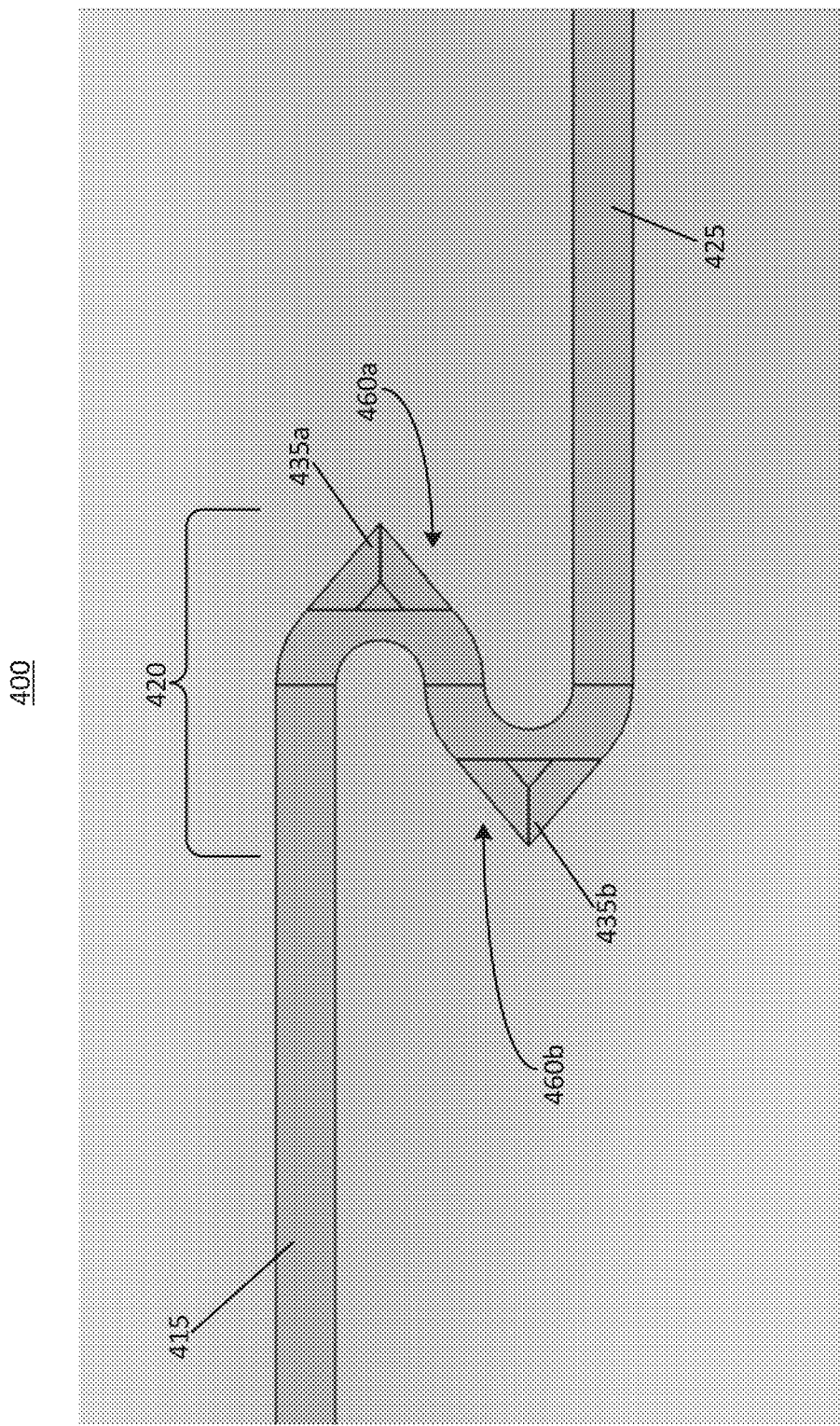
FIG. 4A illustrates a cross-sectional view of a portion of an example microfluidic device that can be used to implement the microfluidic device of FIG. 1A, according to an illustrative implementation.

FIG. 4A illustrates a cross-sectional view of a portion of an example microfluidic device 400 that can be used to implement the microfluidic device 100 of FIG. 1A, according to an illustrative implementation. The features of the microfluidic device 400 generally correspond to the features of the microfluidic device 100, and like reference numerals refer to like elements. For example, the microfluidic device 400 includes an inlet channel 415, a tissue trapping region 420, and an outlet channel 425. FIG. 4A shows the structural details of the tissue trapping region 420, which in this example includes a circuitous channel coupled between the inlet channel 415 and the outlet channel 425. The circuitous channel includes a first curved portion 460a and a second curved portion 460b (generally referred to as curved portions 460). The curvature of the first curved portion 460a is opposed to the curvature of the second curved portion 460b. The first curved portion 460a includes a first tissue trap 435a positioned at its center. The second curved portion 460b is coupled to a downstream end of the first curved portion 460a, and includes a second tissue trap 435b positioned at its center. The first tissue trap 435a and the second tissue trap 435b are generally referred to as tissue traps 435 in this disclosure. The downstream end of the second curved portion 460b is coupled to the outlet channel 425.

While the depiction of FIG. 4A shows the circuitous channel as including two curved portions 460a and 460b, it should be understood that, in other implementations, the circuitous channel may include any number of curved portions each defining a respective tissue trap 435 without departing from the scope of this disclosure. For example, the circuitous channel may include only a single curved portion (i.e., the first curved portion 460a), or may include three or more curved portions.

Similar to the tissue trapping regions 220 shown in FIG. 2A and 320 shown in FIG. 3A, the tissue trapping region 420 (including the tissue traps 435) can be configured to trap a tissue sample in a fixed location while a fluid sample is flowed through the microfluidic device 400. For example, the tissue trapping region 420 is shaped such that, when the fluid sample flows through the microfluidic device 400, a respective tissue sample can become trapped in the tissue traps 435. In some implementations, a separate tissue sample can become trapped in each of the tissue traps 435. In some other implementations, one or more of the tissue traps 435 may remain empty.

Figure 4B:
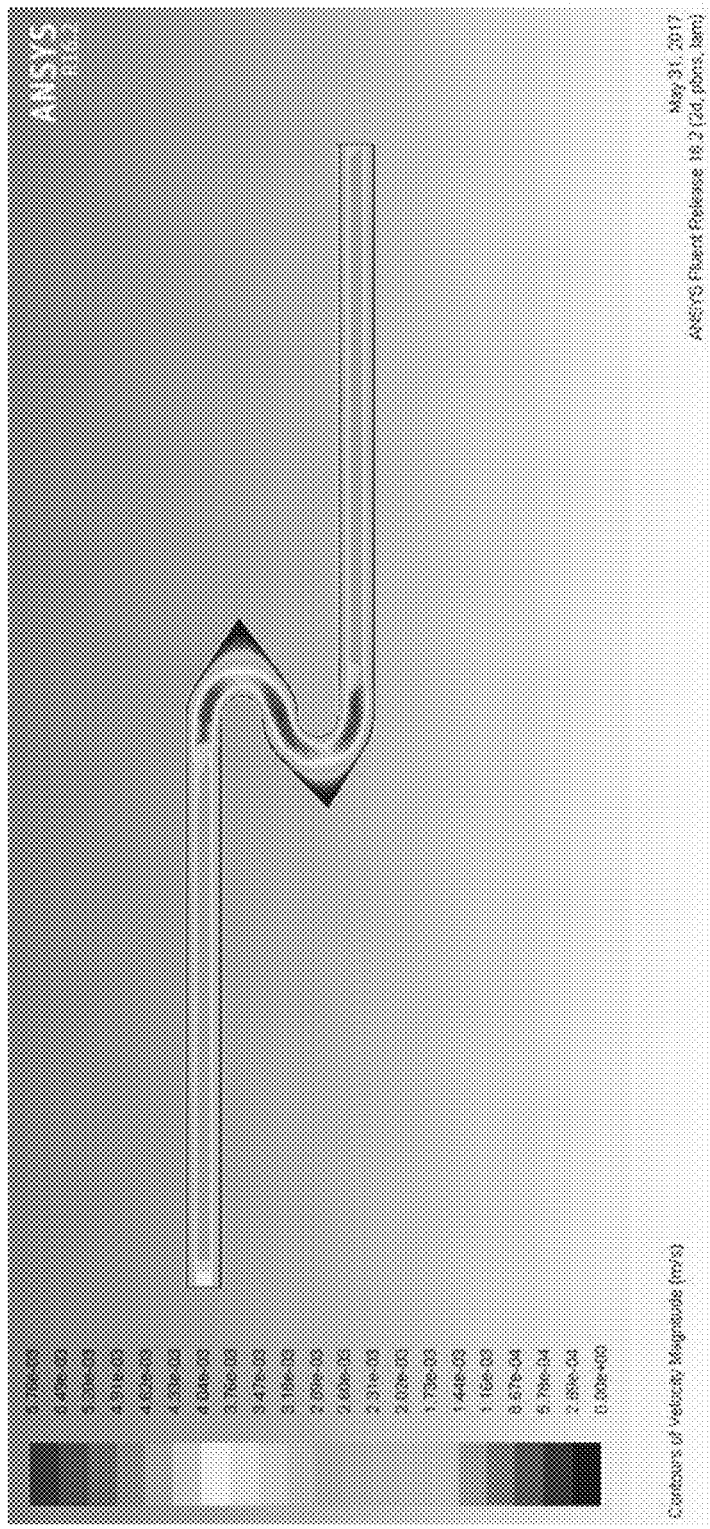
FIG. 4B is a visual depiction of the flow characteristics of the microfluidic device of FIG. 4A, according to an illustrative implementation.

In some implementations, the circuitous shape of the tissue trapping region 420, including the tissue traps 435, is selected to facilitate trapping of a tissue sample while the fluid sample passes through the microfluidic device 300. FIG. 4B is a visual depiction 452 of the flow characteristics of the microfluidic device 400 of FIG. 4A, according to an illustrative implementation. The shading within the channels shows the velocity of the streamlines within the microfluidic device 400. Generally, a particle (such as a tissue sample) in the fluid sample will tend to follow the streamline located at its center of mass. If the Reynolds number of the tissue sample is sufficiently large, the inertia of the particle will overcome the viscous forces when the streamlines bend along the circuitous path including the curved portions 460 of the tissue trapping region 420. As a result, the tissue sample will tend to become secured within the one of the tissue traps 435.

Figure 4C:
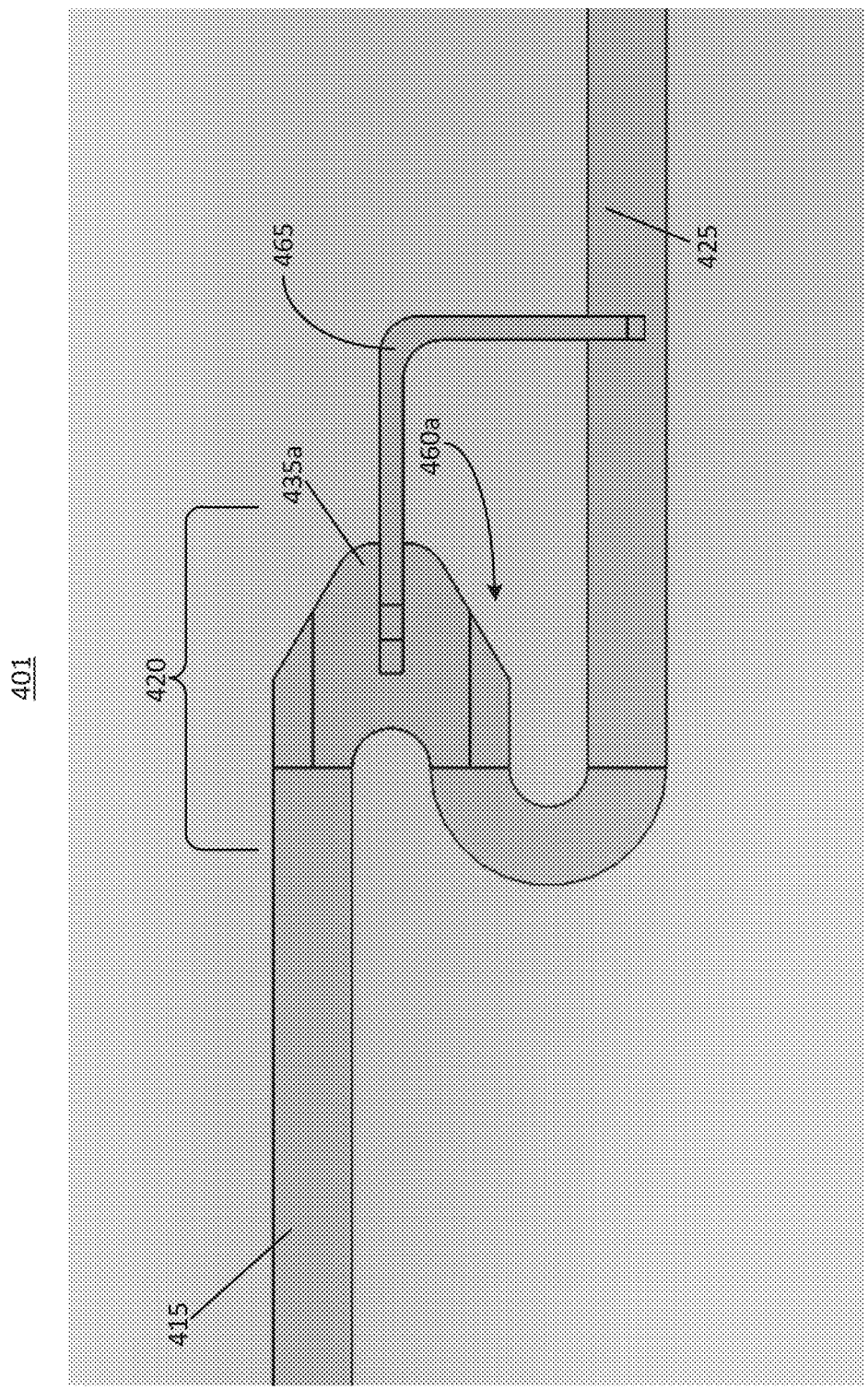
FIG. 4C illustrates a first arrangement of the microfluidic device of FIG. 4A having suction channels, according to an illustrative implementation.
Figure 4D:
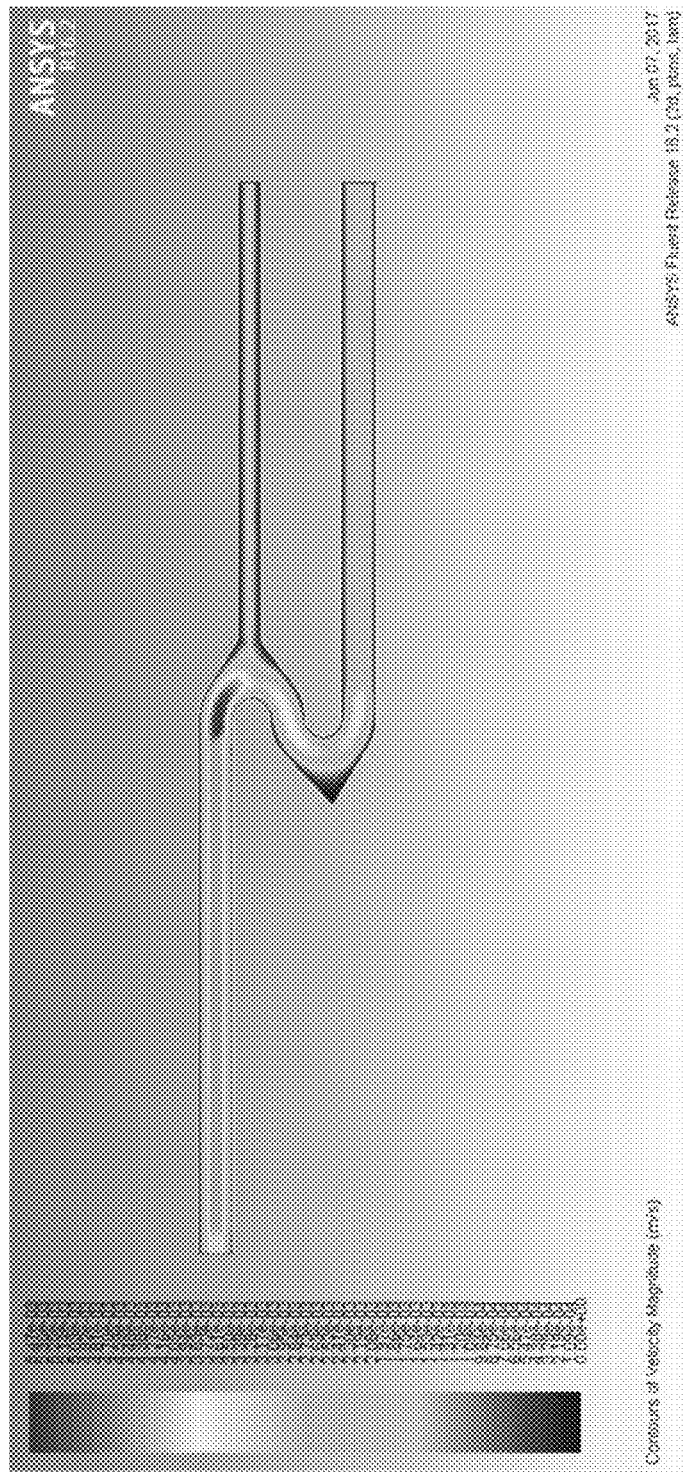
FIG. 4D is a visual depiction of the flow characteristics of the microfluidic device of FIG. 4C, according to an illustrative implementation.

FIG. 4C illustrates a first arrangement 401 of the microfluidic device 400 of FIG. 4A having a suction channel, according to an illustrative implementation. Components shown in the arrangement 401 are substantially similar to the components shown in FIG. 4A, and like reference numerals refer to like elements. However, the arrangement 401 of FIG. 4C differs from that shown in FIG. 4A in that the arrangement 401 includes only a single tissue trap 435a, as well as a suction channel 465. The suction channel 465 is coupled between the tissue trap 435a and the outlet channel 425. In some implementations, the suction channel 465 can be configured to facilitate trapping of the tissue sample within the tissue trap 435a. For example, as the fluid sample flows from left to right in the depiction of FIG. 4D, into the outlet channel 425, the suction channel 465 can create a pressure drop or suction effect that tends to cause the tissue sample to be forced towards the right-hand side of the tissue trap 435a, thereby becoming lodged within the tissue trap 435a more forcefully. FIG. 4D illustrates the flow characteristics of the microfluidic device 401 of FIG. 4C, according to an illustrative implementation. As described in the flow characteristic figures above, the shading in FIG. 4C shows the velocity of the streamlines within the microfluidic device 401. In addition, because the suction channel 465 couples directly to a downstream end of the tissue trap 435a, the suction channel 465 can provide an outlet for fluid in the tissue trap 435a. Therefore, in some implementations the suction channel 465 may sometimes also be referred to as an outlet channel.

FIG. 5 illustrates a bubble trapping structure 110 that can be included in the microfluidic device 100 of FIG. 1A, according to an illustrative implementation. Generally, the bubble trapping structure 110 can help to facilitate the capture of air bubbles from within the fluid sample that flows through the microfluidic device 100, whose presence may be undesirable. Bubbles can be introduced into the microfluidic device 100, for example, during the tissue loading process or via the incoming flow of the fluid sample. In some implementations, bubbles can negatively impact experimental outcomes. Therefore, it may be desirable to prevent air bubbles from entering the system, or to remove them before they reach the tissue sample downstream. Incorporation of an in-line bubble trapping structure 110 into the microfluidic device 100 allows for easy removal of air introduced by either mechanism As shown, the microfluidic device 100 is coupled to a ceiling of the inlet channel 115. The bubble trapping structure 110 includes sidewalls that curve inwards toward each other in a direction away from the inlet channel 115. As shown in FIG. 1A, the bubble trapping structure 110 can be positioned downstream from the inlet port 105, such that air bubbles introduced through the inlet port 105 can be removed via the bubble trapping structure 110 before they reach the tissue trapping region 120. In some implementations, the shape of the sidewalls of the bubble trapping structure 110 can be defined by a parabolic function. The microfluidic device 100 also includes a threaded connector 510. The threaded connector 510 can be configured for attachment to an air line, through which air bubbles can be removed from the device after being captured by the bubble trapping structure 110.

The bubble trapping structure 110 is incorporated directly into the microfluidic device 100. This design eliminates the need for an external air removal device, thereby reducing the number of required connections. Additionally, inclusion of the bubble trapping structure 110 within the microfluidic device 100 can reduce the overall fluid volume requirement. In some implementations, the bubble trapping structure 110 can be configured to produce limited disruption of the primary flow path of the fluid sample through the inlet channel 115. For example, the parabolic curvature of the bubble trapping structure 110 can encourage the gentle removal of bubbles from the flow, and the threaded connector 510, which can couple to an air line or a syringe, allows evacuation of air from the chimney as needed.

In some implementations, the bubble trapping structure 110 also can be configured to serve as the loading port for the tissue sample. For example, the opening of the bubble trapping structure 110 can be configured to accommodate a pipette tip through which the tissue sample is introduced into the microfluidic device 100. In some implementations, the tissue sample can be injected through the bubble trapping structure 110, which may include a valve that can be closed after that tissue sample is injected. Flow of the fluid sample from the inlet port 105 can then cause the tissue sample to flow towards the tissue trapping region 120, where it becomes secured in place as described above.

FIG. 6 illustrates a flowchart of a method 600 for evaluating an interaction between a tissue sample and a fluid sample, according to an illustrative implementation. In some implementations, the method 600 can be carried out using a microfluidic device such as the microfluidic device 100 shown in FIG. 1A. In brief overview, the method 600 can include introducing a tissue sample into an inlet channel of a microfluidic device (step 605), introducing a fluid sample into the inlet channel to cause the tissue sample to flow to a tissue trapping region of the microfluidic device (step 610), collecting the sample fluid from one or more channels providing an outlet downstream from the tissue trapping region (step 615), and observing an interaction between the tissue sample and the fluid sample in the tissue trapping region (step 620).

Referring again to FIG. 6, the method 600 can include introducing a tissue sample into an inlet channel of a microfluidic device (step 605). In some implementations, the tissue sample can be or can include a portion of a tumor or other cancerous cells whose reaction to an immunotherapy is of interest. The tissue sample can be injected into the microfluidic device, for example via a port configured to serve as a bubble trapping structure similar to that shown in FIG. 5. In some implementations, the inlet channel can first be primed with a fluid before the tissue sample is introduced. This can allow the tissue sample to be introduced directly into a fluid, which may help to better preserve the tissue sample for experimentation.

The method 600 also can include introducing a fluid sample into the inlet channel to cause the tissue sample to flow to a tissue trapping region of the microfluidic device (step 610). In some implementations, the fluid sample can include cells, medications, therapeutic compounds, or other components. In some implementations, the fluid sample can be introduced at an area of the inlet channel upstream from the area where the tissue sample was introduced. For example, referring to the microfluidic device 100 of FIG. 1A, the tissue sample can be introduced via the bubble trapping structure 110, and the fluid sample can be introduced at the inlet port 105, upstream from the bubble trapping structure 110. This tissue sample and fluid sample introduction technique can help to ensure that the fluid sample is able to carry the tissue towards the tissue trapping region, which can be downstream from the areas in which both the fluid sample and the tissue sample are introduced.

In some implementations, the tissue trapping region can include at least one tissue trap configured to trap the tissue sample. The tissue trap can include an intersection or junction of one or more fluidly connected channels, cavities, spaces, or chambers. In some implementations, the geometry of the tissue trap can result in a stagnation zone configured such that the fluid flow characteristics in the stagnation zone are relatively stagnant (i.e., fluid velocity is lower, and in some cases may be zero) as compared with the fluid flow characteristics of other portions of the microfluidic device.

In some implementations, the tissue trap can be positioned at an intersection of a relatively large inlet channel and one or more relatively smaller branching channels that carry fluid away from the tissue trap to an outlet channel, for example as illustrated by the tissue trap 235 shown in FIG. 2A. Other structural features also may contribute to the functionality of the tissue trap. For example, in some implementations the tissue trap can include an elevation change relative to the channels that couple to it, such that tissue trap serves as a sunken pocket for receiving and securing the tissue sample. As a result, in some implementations, the tissue trap may sometimes be referred to as a tissue trapping pocket. In some implementations, other walls of the tissue trap also may be stepped away, stepped up or stepped down from the walls of channels that lead to them. For example, a ceiling of the tissue trap may be positioned at an elevated height relative to the ceiling of the inlet channel, and the sidewalls of the tissue trap may be farther apart from one another than the sidewalls of the inlet channel.

In addition, the branching channels carrying fluid away from the tissue trap, as well as the outlet channel, can have a size that helps to trap the tissue sample within the tissue trap. For example, the branching channels and the outlet channel can be sized such that tissue samples larger than about 300 microns cannot progress to the outlet of the microfluidic device from the tissue trap. Thus, the tissue sample can become secured within the tissue trap, such that the cells in the fluid sample can contact the tissue sample as the fluid sample flows through the microfluidic device.

In some implementations, the tissue trap or trapping zone can have a geometry that is selected and/or arranged to trap the tissue sample without damaging the tissue sample. The tissue trap or trapping zone may be formed in any geometrical shape or combination of geometries. The tissue trap may be formed as a chamber or portion of a chamber and in some implementations may be referred to as a trapping chamber. The tissue trap may be formed as any type of pocket, such as a partial pocket or a covered pocket, and in some implementations may be referred to as a trapping pocket. The tissue trap may be formed as any type of cavity and may be referred to as a trapping cavity in some implementations. The tissue trap may be designed, configured and formed such as to provide a pressure drop or suction effect with respect to fluid sample flows traversing an opening of the tissue trap and in some implementations, may be referred to as a pressure drop trap, suction trap or tissue pressure drop zone or tissue suction zone.

The tissue trap may be formed as an arrangement of one or more walls. The one or more walls may be selected designed or configured with predetermined heights and/or lengths and/or widths, such as in relation to any of the dimensions of the device comprising the tissue trap. The one or more walls may be formed to meet at predetermined angles and/or predetermined points, such as in relation to any of the dimensions or geometries of the device comprising the tissue trap. The one or walls may be formed to be at predetermined orientations with respect to other walls and/or other walls of the device comprising the tissue trap. For example, the tissue trap can include one or more walls configured to secure the tissue sample. The walls may be formed from the edges of channels that are in fluid communication with the tissue trap, or may be formed from the edges of the tissue trap itself. In some implementations, a wall included in a tissue trap can be a sidewall, a bottom surface, or a ceiling. In some implementations, the tissue trap may include a curved wall, or may include two or more substantially flat walls that couple to one another at an edge. A wall included in a tissue trap can be configured to restrict the motion of a tissue sample without shearing, tearing, or otherwise damaging the tissue sample, in contrast to other types of structures that may be designed to trap a tissue sample. For example, while a series of narrow posts may be used to secure a tissue sample at a particular point within a microfluidic device, the relatively small width of such posts relative to the width of the tissue sample can cause the tissue sample to become torn by the posts as fluid pressure is exerted on the tissue sample by the fluid flowing through the device. Because a wall has a larger surface area than such a post, the tissue traps described in this disclosure can secure a tissue sample while substantially reducing the risk that the tissue sample will become torn or damaged.

In some implementations, a tissue trap also may include one or more channels, such as suction channels, that exit from a rear surface of the tissue trap and join with branching channels and or an outlet channel downstream from the tissue trap. Examples of such suction channels are illustrated in by the suction channels 240a and 240b of FIGS. 2D-2F and the suction channel 465 of FIG. 4C. As fluid flows through the microfluidic device, such suction channels can cause a pressure drop or other suction force to more securely trap a tissue sample within the tissue trap. Thus, in some implementations, the tissue trap may be referred to as a suction trap. Examples of suitable geometries for such a tissue trap have been described above, for example in connection with FIGS. 1A, 2A, 3A, and 4A.

The method 600 also can include collecting the sample fluid from one or more channels providing an outlet downstream from the tissue trapping region (step 615). In some implementations, the microfluidic device can include an outlet port coupled to an outlet channel and configured to allow the fluid sample to be collected. For example, the outlet port can include a threaded connector, which can be coupled to a fluid line or a syringe to extract the fluid sample. In some implementations, the air bubbles also can be extracted from the fluid sample. For example, air bubbles can be extracted via a bubble trapping structure such as the bubble trapping structure 110 shown in FIG. 5. In some implementations, the bubble trapping structure can be positioned upstream from the tissue trapping region, such that air bubbles can be extracted from the fluid sample before they reach the tissue trapping region.

In some implementations, the method 600 also can include reintroducing the collected sample fluid into the inlet channel of the microfluidic device. That is, the fluid sample can be recirculated one or more times through the microfluidic device. For example, the fluid sample can be introduced into the microfluidic device at step 610 and can be collected at step 615. Then, the same fluid sample can be recirculated through the microfluidic device by reintroducing the fluid sample back into the inlet channel of the microfluidic device, and again collecting the fluid sample from the one or more channels providing the outlet. In some implementations, steps 610 and 615 of the method 600 can be iterated any number of times.

The method 600 also can also include observing an interaction between the tissue sample and the fluid sample in the tissue trapping region (step 620). Because the microfluidic device as described in this disclosure can be configured to simulate the dynamics of tissue-cell interactions that occur in vivo, the observation of the interaction between the tissue sample and the fluid sample can provide valuable insights into the way in which a patient will respond to a particular immunotherapy. In some implementations, the microfluidic device can be formed form a transparent and/or optically clear material, and can be sufficiently thin to permit observation of the interaction between the tissue sample and the fluid sample by external equipment. For example, the microfluidic device can include an optical interface positioned near the tissue trapping region, to allow a microscope, camera, or other optical equipment to be used to observe the interaction that takes place in the tissue trapping region from outside of the microfluidic device. In some implementations, at least one the tissue sample and the fluid sample can include fluorescent particles that may be observed by such optical equipment.

In some implementations, the method 600 also can include releasing the tissue sample from the tissue trap. To release the tissue sample, in some implementations a second fluid sample can be introduced into the one or more channels providing the outlet. This can cause the second fluid sample to flow towards the inlet channel. This reverse flow of fluid can exert fluid forces on the tissue sample within the tissue trap that tend to dislodge the tissue sample from the tissue trap. In some implementations, the tissue sample may be brought to an inlet port of the microfluidic device in this manner, and may be collected and removed from the device at the inlet port.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed only in connection with one implementation are not intended to be excluded from a similar role in other implementations.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

The invention claimed is:

1. A microfluidic device comprising:
    a substrate defining:
        an inlet channel having a first end configured to receive a fluid sample optionally containing a tissue sample;

a tissue trapping region at a second end of the inlet channel downstream from the first end, the tissue trapping region including one or more tissue traps configured to catch the tissue sample flowing through the inlet channel such that the fluid sample contacts the one or more tissue traps;

a first branch channel coupled to the second end of the inlet channel at a first junction and configured to direct a first portion of the fluid sample in a first direction;

a second branch channel coupled to the second end of the inlet channel at the first junction and configured to direct a second portion of the fluid sample in a second direction, different from the first direction, wherein at least one of the one or more tissue traps is positioned at the first junction;

a first suction channel coupling at least one of the one or more tissue traps to the first branch channel at a third junction downstream from the second end of the inlet channel; and a second suction channel coupling at least one of the one or more tissue traps to the second branch channel at a fourth junction downstream from the second end of the inlet channel.

2. The microfluidic device of claim 1, wherein at least one of the one or more tissue traps comprises an arrangement of one or more walls.

3. The microfluidic device of claim 1, wherein at least one of the one or more tissue traps includes a bottom surface positioned at a lower depth than a bottom surface of the inlet channel.

4. The microfluidic device of claim 1, wherein the first branch channel and the second branch channel converge at a second junction downstream from the one or more tissue traps.

5. The microfluidic device of claim 1, wherein a diameter of at least one of the one or more tissue traps is about twice that of the inlet channel.

6. The microfluidic device of claim 1, further comprising an inlet port coupled to the first end of the inlet channel and configured to deliver the fluid sample to the inlet channel.

7. The microfluidic device of claim 6, wherein the inlet port comprises a first threaded connector configured for attachment to a fluid line.

8. The microfluidic device of claim 6, further comprising a bubble trapping structure coupled to the inlet channel downstream from the inlet port, the bubble trapping structure configured to facilitate evacuation of air bubbles from the fluid sample.

9. The microfluidic device of claim 8, wherein a surface of the bubble trapping structure has a shape defined by a parabolic function.

10. The microfluidic device of claim 8, wherein the bubble trapping structure further comprises a second threaded connector configured for attachment to an air release line.

11. The microfluidic device of claim 1, further comprising an outlet port coupled to at least one of the first branch channel or the second branch channel providing an outlet and configured to remove the fluid sample from the microfluidic device.

12. The microfluidic device of claim 1, wherein the substrate is formed from a biocompatible material.

13. The microfluidic device of claim 1, wherein the substrate is formed from an optically transparent material, the microfluidic device further comprising:

an optical interface providing optical access to the tissue sample positioned within the tissue trapping region.

14. The microfluidic device of claim 1, wherein the one or more tissue traps are configured to entrain the tissue sample in place within the one or more tissue traps.

15. A microfluidic device, comprising:
a substrate defining:
an inlet channel having a first end configured to receive a fluid sample;
a tissue trapping region at a second end of the inlet channel downstream from the first end, the tissue trapping region including one or more tissue traps configured to catch a tissue sample flowing through the inlet channel such that the fluid sample contacts the one or more tissue traps;
wherein at least one of the one or more tissue traps comprises a bottom surface defined at a lower depth in the substrate than a bottom surface of the inlet channel defined in the substrate; and
one or more channels providing an outlet, the one or more channels comprising one or more suction channels downstream from the one or more tissue traps and configured to hold the tissue sample in place within the lower depth of the one or more tissue traps.

16. The microfluidic device of claim 15, wherein at least one of the one or more tissue traps comprises an arrangement of one or more walls.

17. The microfluidic device of claim 15, wherein the one or more channels providing the outlet comprise one or more branch channels connecting to the second end of the inlet channel where the second end of the inlet channel and the tissue trapping region converge.

18. The microfluidic device of claim 17, wherein the convergence of the second end of the inlet channel and the tissue trapping region further comprises:

a first branch channel coupled to the second end of the inlet channel at a first junction and configured to direct a first portion of the fluid sample in a first direction; and a second branch channel coupled to the second end of the inlet channel at the first junction and configured to direct a second portion of the fluid sample in a second direction, different from the first direction, wherein at least one of the one or more tissue traps is positioned at the first junction.

19. The microfluidic device of claim 18, wherein the first branch channel and the second branch channel converge at a second junction downstream from the one or more tissue traps.

20. The microfluidic device of claim 18, further comprising:

a first suction channel coupling at least one of the one or more tissue traps to the first branch channel at a third junction downstream from the second end of the inlet channel; and a second suction channel coupling the at least one of the one or more tissue traps to the second branch channel at a fourth junction downstream from the second end of the inlet channel.

21. The microfluidic device of claim 18, wherein a diameter of at least one of the one or more tissue traps is about twice that of the inlet channel.

22. The microfluidic device of claim 15, further comprising an inlet port coupled to the first end of the inlet channel and configured to deliver the fluid sample to the inlet channel.

23. The microfluidic device of claim 22, further comprising a bubble trapping structure coupled to the inlet channel downstream from the inlet port, the bubble trapping structure configured to facilitate evacuation of air bubbles from the fluid sample.

24. The microfluidic device of claim 22, wherein the inlet port comprises a first threaded connector configured for attachment to a fluid line.

25. The microfluidic device of claim 23, wherein a surface of the bubble trapping structure has a shape defined in part by a parabolic function.

26. The microfluidic device of claim 23, wherein the bubble trapping structure further comprises a second threaded connector configured for attachment to an air release line.

27. The microfluidic device of claim 15, wherein the substrate is formed from a biocompatible material.

28. The microfluidic device of claim 15, wherein the substrate is formed from an optically transparent material, and the microfluidic device further comprises an optical interface providing optical access to the tissue sample positioned within the tissue trapping region.

29. The microfluidic device of claim 15, wherein the one or more tissue traps are configured to entrain the tissue sample in place within the one or more tissue traps.

\* \* \* \* \*